United States Patent [19]

Rentzea et al.

[11] Patent Number: 5,637,554
[45] Date of Patent: Jun. 10, 1997

[54] 5-SUBSTITUTED 4-METHYL-5H-INDENO[3,2-B]PYRIDINES AND 9-SUBSTITUTED 1-METHYL-9H-INDENO[2,3-C]PYRIDINES, THEIR PREPARATION AND USE AS HERBICIDES AND PLANT GROWTH REGULATORS

[75] Inventors: Costin Rentzea, Heidelberg; Norbert Meyer, Ladenburg; Juergen Kast, Boehl-Iggelheim; Peter Plath, Frankenthal; Hartmann Koenig, Limburgerhof; Albrecht Harreus, Ludwigshafen; Uwe Kardorff, Mannheim; Matthias Gerber, Limburgerhof; Helmut Walter, Obrigheim; Andreas Landes, Limburgerhof; Karl-Otto Westphalen, Speyer, all of Germany

[73] Assignee: BASF Aktiengesellschaft, Ludwigshafen, Germany

[21] Appl. No.: 433,472

[22] PCT Filed: Jan. 12, 1994

[86] PCT No.: PCT/EP94/00071

§ 371 Date: May 12, 1995

§ 102(e) Date: May 12, 1995

[87] PCT Pub. No.: WO94/17044

PCT Pub. Date: Aug. 4, 1994

[30] Foreign Application Priority Data

Jan. 20, 1993 [DE] Germany ............... 43 01 426.7

[51] Int. Cl.[6] .................. A01N 43/42; C07D 221/16
[52] U.S. Cl. ................................ 504/245; 546/111
[58] Field of Search ....................... 546/111; 504/245

[56] References Cited

U.S. PATENT DOCUMENTS 4,873,250  10/1989  Hufford ............................. 514/290

FOREIGN PATENT DOCUMENTS

| 369426 | 5/1990 | European Pat. Off. |
| 3161478-A | 7/1991 | Japan. |
| 2223946 | 4/1990 | United Kingdom. |
| 93/21162 | 10/1993 | WIPO. |

OTHER PUBLICATIONS

Hufford CD, Liu S, Clark A. (1987) J. Nat. Prod. 50 (5) 961–964.

Arango GJ, Cortes D, Cassels BK, Cave A, Merienne C. (1987) Phytochemistry 26(7) 2093–2098.

Chem. Abst., vol. 57, No. 2, Jul. 23, 1962.

Primary Examiner—C. Warren Ivy
Assistant Examiner—Evelyn Huang
Attorney, Agent, or Firm—Keil & Weinkauf

[57] ABSTRACT

A method for controlling undesired plant growth and for regulating plant growth by allowing 4-methyl-5H-indeno[3,2-b]pyridines and 1-methyl-9H-indeno[2,3-c]pyridines of the general formula I

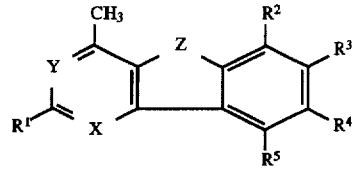

where X, Y, Z and the radicals $R^1$ to $R^5$ have the meanings as described in the specification, to act on the plants, and novel 4-methyl-5H-indeno-[3,2-b]pyridines and herbicides and plant growth regulators containing these.

6 Claims, No Drawings

5-SUBSTITUTED 4-METHYL-5H-INDENO[3,2-B]PYRIDINES AND 9-SUBSTITUTED 1-METHYL-9H-INDENO[2,3-C]PYRIDINES, THEIR PREPARATION AND USE AS HERBICIDES AND PLANT GROWTH REGULATORS

This application is the national phase of PCT/EP94/00071 filed on Jan. 12, 1994.

The present invention relates to 4-methyl-5H-indeno[3,2-b]pyridines and 1-methyl-9H-indeno[2,3-c]pyridines of the formula I

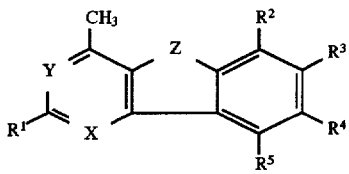

where X, Y, Z and the radicals $R^1$ to $R^5$ have the following meanings:

$R^1$ is hydrogen, $C_1$-$C_6$-alkyl or a $COR^6$ group, $R^6$ being $C_1$-$C_4$-alkyl, $R^2$-$R^5$ are
- a) hydrogen,
- b) halogen,
- c) nitro,
- d) $COOR^6$, $R^6$ being $C_1$-$C_4$-alkyl,
- e) $CONH_2$ or $CONR^6R^7$, $R^6$ and $R^7$ being $C_1$-$C_4$-alkyl,
- f) $C_1$-$C_8$-alkyl which can carry one to three of the following substituents: halogen, hydroxyl or $C_1$-$C_6$-alkoxy,
- g) $C_3$-$C_6$-alkenyl,
- h) $C_1$-$C_4$-alkoxy,
- i) hydroxyl,
- j) amino or $NR^6R^7$,
- k) phenyl which can carry one to five halogen atoms or one to three of the following substituents: nitro, $C_1$-$C_4$-alkoxy, $C_1$-$C_4$-alkyl or $C_1$-$C_4$-haloalkyl;

X and Y are N, $N^+$—$O^-$ or $CR^8$, $R^8$ being hydrogen, $C_1$-$C_2$-alkyl, COOH or $COOR^6$, with the proviso that exclusively one nitrogen atom or one N-oxide group is contained in the ring;

Z is a C═O, CH—$OR^9$, CH—O—$COR^9$ or C═N—W—$R^9$ group, W being oxygen or the —$N(R^{10})$ group and where $R^9$ is hydrogen, a $C_1$-$C_6$-alkyl group which can be substituted by halogen, $COOR^6$ or $C_1$-$C_4$-alkoxy, a $C_3$-$C_6$-alkenyl group, a $C_3$-$C_6$-haloalkenyl group, a $C_3$-$C_6$-alkynyl group, or phenyl, phenyl-$C_1$-$C_4$-alkyl or mononuclear heteroaryl or heteroaryl-$C_1$-$C_4$-alkyl radicals, these aromatic or heteroaromatic groups being able to carry one to three of the following substituents on the ring: halogen, nitro, $C_1$-$C_6$-alkyl, $C_1$-$C_6$-alkoxy, $C_1$-$C_2$-haloalkyl, amino, $C_1$-$C_6$-alkylamino or di($C_1$-$C_6$-alkyl)amino and $R^{10}$ is hydrogen or a $C_1$-$C_4$-alkyl group, and the salts of I with those acids which do not adversely affect the herbicidal or the plant growth-regulating action of I, excluding onychine, 6-, 7-, 8- and 9-methoxyonychine, 6-, 7-, 8- and 9-hydroxyonychine, 7,8-dimethoxyonychine and 4-methyl-5H-indeno-[3,2-b]pyridines of the formula Ia

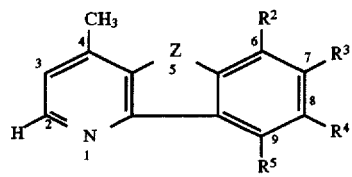

where two of the radicals $R^2$, $R^3$, $R^4$ and $R^5$ form a combination of methoxy and hydroxyl if Z is C═O or CHOH and the remaining two radicals are hydrogen or methoxy.

The alkaloid onychine or 4-methyl-5H-indeno[3,2-b]pyridin-5-one, which was isolated from the plant *Onychopetalum amazonicum*, is known from the investigations of J. Koyama et al. (Heterocycles 12 (1979), 1017–1019) and V. Sniekus et al. (Tetrahedron Lett., 29 (1988), 2135–2136). Other alkaloids structurally related to onychine, such as, for example, 8-methoxyonychine (M. O. F. Goulart et al., Phytochemistry 25 (1986), 1691–95 and Phytochemistry 26 (1987), 1551–1552) isolated from *Guatteria dielsiana*, kinabaline or 6,9-dimethoxy-8-hydroxyonychine (D. Tadic et al., Phytochemistry 26 (1987), 537–541) from *Meiogyne virgata*, darienine or 8,9-dimethoxy-7-hydroxyonychine and macondine or 6-methoxy-7-hydroxyonychine (A. Cave et al., Phytochemistry 26 (1987), 2093–2098) from *Oxandra xylopioides*, ursuline or 8-hydroxy-9-methoxyonychine and isoursuline or oxylopine or 9-hydroxy-8-methoxy-onychine (A. Cave et al., Heterocycles 27 (1988), 407–421) from *Unonopsis spectabilis*, polylongine or 4-methyl-9-hydroxy-8-methoxy-5H-indeno[3,2-b]pyridin-5-ol (Yang Chang Wu, Heterocycles 29 (1989), 463–475) from *Polyalthia longifolia*, oncodine or 7-methoxy-8-hydroxyonychine (A. Cave et al., J. Natural Prod., 52 (1989), 273–278) from *Oncostigma monosperma* and polyfothine or 7,8-dimethoxyonychine and isooncodine or 7-hydroxy-8-methoxyonychine (Yang Chang Wu et al., J. Natural Prod., 53 (1990), 1327–1331) from *Polyalthia longifolia* are also already known.

In the literature mentioned, these alkaloids are ascribed antitumor, antiviral, anticandidal and fungicidal properties. A herbicidal or plant-growth regulating action of these natural substances is not known however.

It is furthermore known that certain indenopyridazines (JO 3161478-A) and indenopyrazoles (GB-A-2 223 946) have herbicidal properties.

As the known natural substances are not always satisfactory in their action, it was the object of the invention to make available novel herbicidal agents having a stronger herbicidal effect and novel plant growth regulators, preferably growth inhibitors. An object of the invention was furthermore novel herbicidal and plant growth-regulating compounds.

We have found that this object is achieved by the novel compounds I defined at the outset.

The invention furthermore relates to herbicidal and bioregulatory, in particular plant growth-inhibiting, compositions, containing the compounds I and processes for preparing the compounds I. Moreover, it was found that the compounds of the formula Ia, which correspond to the compounds of the formula I, are particularly suitable for use as herbicides or plant growth regulators.

Preferred compounds of the formula I are those where the substituents have the following meanings:

$R^1$ is hydrogen, $C_1$-$C_6$-alkyl, in particular $C_1$-$C_4$-alkyl, eg. methyl, ethyl, propyl and $COR^6$ such as acetyl;

$R^2$, $R^3$, $R^4$ and $R^5$ are hydrogen, fluorine, chlorine, bromine, unbranched or branched $C_1$-$C_8$-alkyl, in particular $C_1$-$C_6$-alkyl such as methyl, ethyl, n-propyl, isopropyl, n-butyl, sec-butyl, isobutyl, tert-butyl, n-pentyl, isopentyl, 1,1-dimethylpropyl, 2,2-dimethylpropyl, n-hexyl or 1-ethyl-1-methylpropyl, an unbranched or branched $C_1$-$C_8$-alkyl group, in particular a $C_1$-$C_6$-alkyl group which can carry up to 3 of the following substituents: halogen such as fluorine, chlorine or bromine, hydroxyl, $C_1$-$C_6$-alkoxy such as methoxy, ethoxy and propoxy;

an unbranched or branched $C_3$-$C_6$-alkenyl group, in particular vinyl, allyl, 2-methylallyl, 3-methylallyl, 2,3-dimethylallyl, 3,3-dimethylallyl, 2-pentenyl and 3-pentenyl;

a $C_1$-$C_4$-alkoxy group, in particular methoxy, ethoxy and propoxy, nitro, amino ($NH_2$), ester groups such as eg. $COOCH_3$, $COOC_2H_5$ or $COOC_3H_7$; amides such as $CO$—$NH_2$ or $CO$—$N(CH_3)_2$ and $CO$—$N(C_2H_5)_2$;

a phenyl group, unsubstituted or mono- to trisubstituted by fluorine, chlorine, $CF_3$, $NO_2$ or $C_1$-$C_4$-alkyl;

$R^6$ and $R^7$ are an unbranched or branched $C_1$-$C_4$-alkyl group such as methyl, ethyl, n-propyl, isopropyl, n-butyl, isobutyl, sec-butyl or tert-butyl;

$R^8$ is hydrogen, methyl, ethyl, COOH, $COOCH_3$, $COOC_2H_5$ and $COOC_3H_7$;

$R^9$ is hydrogen, $C_1$-$C_6$-alkyl such as methyl, ethyl, n-propyl, isopropyl, n-butyl, isobutyl, sec-butyl, tert-butyl, n-pentyl, isopentyl and n-hexyl, it being possible for the alkyl group to be substituted by halogen such as fluorine, chlorine, bromine or iodine, methoxy, ethoxy or $COOCH_3$ or $COOC_2H_5$;

$C_3$-$C_6$-alkenyl such as ethenyl, 2-propenyl, 2-butenyl, 2-methyl-2-propenyl, 3-butenyl, 2-pentenyl, 3-methyl-2-butenyl and 3-pentenyl;

$C_3$-$C_6$-haloalkenyl such as 2-chloro-2-propenyl, 3-chloro-2-propenyl, 2-bromo-2-propenyl, 3-chloro-2-butenyl and 2,3,3-trichloro-2-propenyl;

the phenyl or phenyl-$C_1$-$C_4$-alkyl group or a mononuclear heteroaryl or heteroaryl-$C_1$-$C_4$-alkyl radical, heteroaryl in each case being a heteroaromatic radical having 5 to 6 ring members, containing 1 to 3 heteroatoms such as N, S or O. Examples which may be mentioned are 2-pyrrolyl, 2-thienyl, 3-thienyl, 3-furanyl, 4-pyridyl, 3-pyridyl, 2-pyridyl, 2-thiazolyl or 3-, 4- or 5-isoxazolyl.

The abovementioned aromatic and heteroaromatic groups can contain one to three of the following substituents: halogen such as fluorine, chlorine and bromine, nitro, $C_1$-$C_6$-alkyl such as methyl, ethyl, n-propyl, isopropyl, n-butyl, isobutyl, sec-butyl, tert-butyl, n-pentyl, isopentyl, $C_1$-$C_6$-alkoxy such as methoxy, ethoxy, propoxy, n-butoxy, isobutoxy and tert-butoxy, $C_1$-$C_2$-haloalkyl such as trifluoromethyl or trichloromethyl and amino, $C_1$-$C_6$-alkylamino such as methylamino and ethylamino or di-($C_1$-$C_6$) alkylamino such as dimethylamino;

$R^{10}$ is hydrogen, methyl, ethyl or propyl;

X is N, $N^+$—$O^-$ or C—$R^8$;

Y is CH or N;

Z is a C=O, CH—$OR^9$, CH—O—$COR^9$ or C=N—W—$R^9$ group,

W is oxygen or the —$N(R^{10})$ group.

Preferred novel indenopyridines of the formula I are listed in Tables 1 and 2.

Suitable acid addition salts are the salts of those acids which do not adversely affect the herbicidal action of the compounds I and Ia, that is eg. the hydrochlorides and bromides, sulfates, nitrates, phosphates, oxalates or dodecylbenzenesulfonates.

The 4-methyl-5H-indeno[3,2-b]pyridines Ia are known or (in the case of I) obtainable in a manner known per se.

In the cases in which Y=CH, X=N, $R^1$=H and Z is the C=O group, the compounds I or Ia can be prepared according to the following scheme:

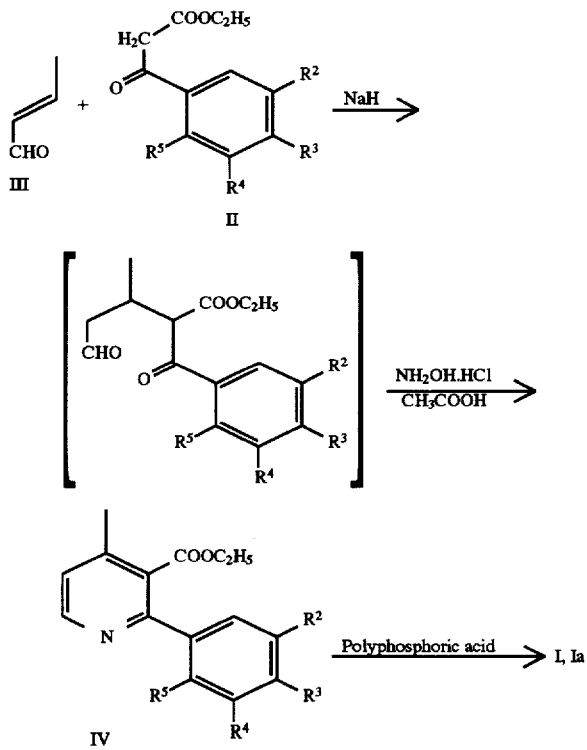

This process is known eg. from the investigations of F. Bracher (Liebigs Ann. Chem., 1988, 87 and Arch. Pharm., 322 (1989), 293).

The Michael addition of the benzoylacetic ester II to crotonaldehyde III is in this case carried out in an inert solvent, eg. in dioxane using an alkali metal hydride, eg. sodium hydride, as a catalyst and the further cyclization to 4-methyl-2-aryl-nicotinic acid ester IV, preferably using hydroxylamine hydrochloride in an organic acid, eg. acetic acid. The following cyclization to the compounds I or Ia using polyphosphoric acid takes place at from 90° to 180° C., preferably at from 100° to 170° C., it advantageously being possible to use the polyphosphoric acid as a solvent and diluent for the reaction. The starting substances necessary for the synthesis are either commercially available or are prepared by generally known processes. They are preferably employed in approximately stoichiometric molar ratios.

In the cases where Y=CH, X=N, $R^1 \neq$ CH and Z is the C=O group, the compounds I and Ia are preferably synthesized by the one-stage process of E. Breitmaier and E. Bayer (Angew. Chem. Int. Ed. Engl., 8 (1969), 865):

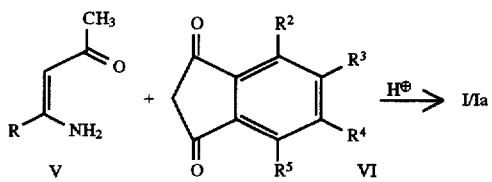

This cyclization is preferably carried out in an acidic medium, eg. in organic acids such as eg. formic acid, acetic acid, propionic acid or trifluoroacetic acid, which may contain up to 30% of water. It may also be advantageous to perform the reaction in the presence of ammonium formate or ammonium acetate or propionate (up to stoichiometric amounts). In general, the reaction temperatures are from 70° to 140° C., preferably from 80° to 130° C.

The enaminones V can be prepared eg. according to P. C. Baraldi et al. (Synthesis, 1983,902) and the dihydroindan-1,3-diones VI eg. according to A. R. Murthy et al., (J. Med. Chem., 28 (1985), 1591).

1-Methyl-9H-indeno[2,3-c]pyridines of the formula I where $R^1 \neq H$, X=CH or COOH, Y=N and Z=the C=O group can be obtained by cyclization of 4-arylnicotinic acid esters or of 4-arylpyridine-3,5-dicarboxylic acid esters in polyphosphoric acid at from 100° to 180° C.:

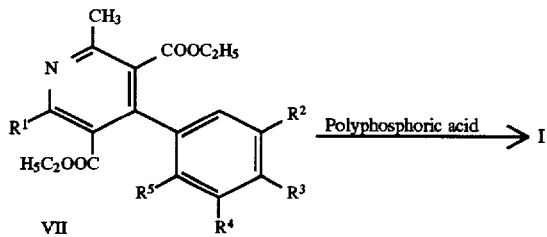

The 4-aryl-3,5-dicarboxylic acid esters VII can be obtained by sodium nitrite oxidation (cf. K. Görlitzer et al., Arch. Pharm. 314 (1981), 949) of the corresponding 1,4-dihydropyridine derivatives, which are in turn accessible by Hantzsch synthesis (see eg. B. Loev et al., J. Med. Chem., 17 (1974), 956).

The synthesis of the compounds I where $X=N^+—O^-$ is carried out by reaction of the corresponding indenopyridines with $H_2O_2$ or with organic peroxy acids according to standard processes (see eg. E. Ochiai, Aromatic Amine Oxides, Elsevier, Amsterdam, 1967, pp. 200–250).

Compounds of the formula I/Ia where Z=CO can be reduced to the corresponding alcohols (Z=CH—OH) using complex hydrides, preferably using sodium borohydride.

The reaction is preferably carried out in a protic diluent such as eg. methanol, ethanol or isopropanol at from -10° to 50° C., preferably from 0° to 30° C.

The ketones of the formula I/Ia can also be reacted with secondary alcoholates (preferably from 0.3 to 1.5 molar equivalents), preferably of aluminum, such as eg. aluminum isopropylate, aluminum 2-butylate or aluminum cyclohexylate in the presence of a diluent at from 60° to 160° C., preferably at the boiling point of the diluent. Suitable diluents are inert organic solvents, in particular low molecular weight alcohols such as isopropanol or cyclohexanol. The resulting alcoholates are then hydrolyzed in the customary manner to the free alcohols of the formula I/Ia with Z=CHOH with the aid of acids.

The process for preparing the esters of the formula I/Ia ($Z=CH—O—COR^9$) consists in reacting the alcohols I/Ia (Z=CH—OH) with the appropriate acid chlorides or acid anhydrides in the presence of an acid acceptor and if appropriate in the presence of an aprotic solvent or diluent, and preferably in the presence of an acylating catalyst, at from 0° to 100° C., preferably from 10° to 50° C. The acid acceptors employed can be inorganic bases such as sodium carbonate, potassium carbonate, sodium hydride or particularly preferably pyridine or triethylamine in at least equivalent amounts. The acylating catalysts used are expediently imidazole or 4-dimethylaminopyridine in quantitative amounts of from 0.01 to 0.4 equivalents, if pyridine is not already present. The solvents employed can be hydrocarbons such as cyclohexane or toluene, ethers such as diethyl ether or tetrahydrofuran or even excess acid acceptor amines such as triethylamine or pyridine.

The preparation of the oximes and of the hydrazones I/Ia ($Z=C=N—W—R^9$) is preferably carried out in alcohols such as methanol, ethanol or isopropanol or in organic acids such as acetic acid or mixtures thereof, at 50°–130° C., preferably at the boiling point of the solvent.

Stoichiometric amounts or a small excess of the O-substituted hydroxylamine or of the hydrazine are preferably employed.

Indenopyridines of the general formula I or Ia which are preferred with respect to biological use are listed in the following Table 1 and in Table 2. Compounds of the formula I are particularly preferred in which at least one (in particular one to three) of the radicals $R^2$-$R^5$ is $C_1$-$C_4$-haloalkyl or halogen, in particular fluorine, chlorine or bromine. Further preferred are compounds where $R^2$, $R^3$, $R^4$ or $R^5$=alkyl, in particular branched alkyl or cycloalkyl such as cyclohexyl, cyclopropyl or cyclopentyl. In addition, compounds are preferred in which 1, 2 or 3 of the radicals $R^2$-$R^5$ are $NO_2$, $NH_2$, $CONH_2$ or phenyl. If not all the radicals $R^2$-$R^5$ are hydrogen, preferably one, two or three substituents on the phenyl ring are not hydrogen.

TABLE 1

| $R^1$ | $R^2$ | $R^3$ | $R^4$ | $R^5$ | X | Y | Z |
|---|---|---|---|---|---|---|---|
| H | H | H | H | H | N | CH | C=O |
| H | H | H | H | H | $N^+$—O | CH | C=O |
| H | H | H | H | H | N | CH | CH—OH |
| H | H | H | H | H | $N^+$—O$^-$ | CH | CH—OH |
| H | H | H | H | H | N | CH | CH—OCH$_3$ |
| H | H | H | H | H | N | CH | CH—OC$_2$H$_5$ |
| H | H | H | H | H | N | CH | CH—OC$_3$H$_7$-n |
| H | H | H | H | H | $N^+$—O$^-$ | CH | CH—OCH$_3$ |
| H | H | H | H | H | $N^+$—O$^-$ | CH | CH—OC$_2$H$_5$ |
| H | H | H | H | H | N | CH | CH—OC$_3$H$_7$-iso |

TABLE 1-continued

| R$^1$ | R$^2$ | R$^3$ | R$^4$ | R$^5$ | X | Y | Z |
|---|---|---|---|---|---|---|---|
| H | H | H | H | H | N | CH | CH—OC$_4$H$_9$-n |
| H | H | H | H | H | N | CH | CH—OC$_4$H$_9$-iso |
| H | H | H | H | H | N | CH | CH—OC$_5$H$_{11}$-n |
| H | H | H | H | H | N | CH | CH—O—CH$_2$—C$_6$H$_5$ |
| H | H | H | H | H | N$^+$—O$^-$ | CH | CH—O—CH$_2$—C$_6$H$_5$ |
| H | H | H | H | H | N | CH | CH—O—CH$_2$CH$_2$—C$_6$H$_5$ |
| H | H | H | H | H | N | CH | CH—O—CH$_2$CH$_2$CH$_2$—C$_6$H$_5$ |
| H | H | H | H | H | N | CH | CH—O—CH$_2$—C$_6$H$_4$-4F |
| H | H | H | H | H | N | CH | CH—O—CH$_2$—C$_6$H$_4$-3F |
| H | H | H | H | H | N | CH | CH—O—CH$_2$—C$_6$H$_4$-2F |
| H | H | H | H | H | N | CH | CH—O—CH$_2$—C$_6$H$_4$-4Cl |
| H | H | H | H | H | N$^+$—O$^-$ | CH | CH—O—CH$_2$—C$_6$H$_4$-4Cl |
| H | H | H | H | H | N | CH | CH—O—CH$_2$—C$_6$H$_4$-Br |
| H | H | H | H | H | N | CH | CH—O—CH$_2$—C$_6$H$_4$-2CH$_3$ |
| H | H | H | H | H | N | CH | CH—O—CH$_2$—C$_6$H$_4$-4CH$_3$ |
| H | H | H | H | H | N$^+$—O$^-$ | CH | CH—O—CH$_2$—C$_6$H$_4$-4-ethyl |
| H | H | H | H | H | N | CH | CH—O—CH$_2$—C$_6$H$_4$-4-tert-butyl |
| H | H | H | H | H | N | CH | CH—O—CH$_2$C$_6$H$_4$-4-n-butyl |
| H | H | H | H | H | N | CH | CH—O—CH$_2$C$_6$H$_4$-4NO$_2$ |
| H | H | H | H | H | N | CH | CH—O—CH$_2$C$_6$H$_4$-4CF$_3$ |
| H | H | H | H | H | N | CH | CH—O—CH$_2$C$_6$H$_4$-4OCH$_3$ |
| H | H | H | H | H | N$^+$—O$^-$ | CH | CH—O—CH$_2$C$_6$H$_4$-4OCH$_3$ |
| H | H | H | H | H | N | CH | CH—O—CH$_2$C$_6$H$_3$-2,4F$_2$ |
| H | H | H | H | H | N | CH | CH—O—CH$_2$C$_6$H$_3$-3,4F$_2$ |
| H | H | H | H | H | N | CH | CH—O—CH$_2$C$_6$H$_3$-2,4Cl$_2$ |
| H | H | H | H | H | N | CH | CH—O—CH$_2$C$_6$H$_3$-3,4Cl$_2$ |
| H | H | H | H | H | N | CH | CH—O—CH$_2$C$_6$H$_3$-3,4(CH$_3$)$_2$ |
| H | H | H | H | H | N | CH | CH—O—CH$_2$C$_6$H$_3$-2,4(CH$_3$)$_2$ |
| H | H | H | H | H | N$^+$—O$^-$ | CH | CH—OCOCH$_3$ |
| H | H | H | H | H | N | CH | CH—OCOCH$_3$ |
| H | H | H | H | H | N | CH | CH—OCOCH$_2$CH$_2$CH$_3$ |
| H | H | H | H | H | N | CH | CH—OCOCH(CH$_3$)$_2$ |
| H | H | H | H | H | N | CH | CH—OCO(CH$_2$)$_3$CH$_3$ |
| H | H | H | H | H | N | CH | CH—OCO(CH$_2$)$_4$CH$_3$ |
| H | H | H | H | H | N | CH | CH—OCOC$_6$H$_5$ |
| H | H | H | H | H | N$^+$—O$^-$ | CH | CH—OCOC$_6$H$_5$ |
| H | H | H | H | H | N | CH | CH—OCOCH$_2$C$_6$H$_5$ |
| H | H | H | H | H | N | CH | CH—OCOCH$_2$CH$_2$C$_6$H$_5$ |
| H | H | H | H | H | N | CH | CH—OCOC$_6$H$_4$-2F |
| H | H | H | H | H | N | CH | CH—OCOC$_6$H$_4$-3F |
| H | H | H | H | H | N | CH | CH—OCOC$_6$H$_4$-4F |
| H | H | H | H | H | N | CH | CH—OCOC$_6$H$_4$-2Cl |
| H | H | H | H | H | N | CH | CH—OCOC$_6$H$_4$-4Cl |
| H | H | H | H | H | N | CH | CH—OCOC$_6$H$_4$-4CF$_3$ |
| H | H | H | H | H | N$^+$—O$^-$ | CH | CH—OCOC$_6$H$_4$-4CF$_3$ |
| H | H | H | H | H | N | CH | CH—OCOC$_6$H$_4$-3CF$_3$ |
| H | H | H | H | H | N$^+$—O$^-$ | CH | CH—OCOC$_6$H$_4$-3CF$_3$ |
| H | H | H | H | H | N | CH | CH—OCO-2-pyridinyl |
| H | H | H | H | H | N | CH | CH—OCO-3-pyridinyl |
| H | H | H | H | H | N | CH | CH—OCO-4-pyridinyl |
| H | H | H | H | H | N$^+$—O$^-$ | CH | CH—OCO-3-pyridinyl |
| H | H | H | H | H | N | CH | CH—OCO-2-thienyl |
| H | H | H | H | H | N | CH | CH—OCO-3-thienyl |
| H | H | H | H | H | N | CH | CH—OCO-(5-F-2-thienyl) |
| H | H | H | H | H | N | CH | CH—OCO-(4-F-2-thienyl) |
| H | H | H | H | H | N | CH | CH—OCO-(3-F-2-thienyl) |
| H | H | H | H | H | N | CH | CH—OCO-(5-Cl-2-thienyl) |
| H | H | H | H | H | N | CH | CH—OCO-(5-Br-2-thienyl) |
| H | H | H | H | H | N | CH | CH—OCO-(5-Cl-3-thienyl) |
| H | H | H | H | H | N | CH | CH—OCO-(5-CH$_3$-2-thienyl) |
| H | H | H | H | H | N | CH | CH—OCO-2-thiazolyl |
| H | H | H | H | H | N | CH | CH—OCO-3-isoxazolyl |
| H | H | H | H | H | N | CH | CH—OCO-4-isoxazolyl |
| H | H | H | H | H | N | CH | CH—OCO-5-isoxazolyl |
| H | H | H | H | H | N | CH | C=N—OH |
| H | H | H | H | H | N | CH | C=N—OCH$_3$ |
| H | H | H | H | H | N | CH | C=N—OC$_2$H$_5$ |
| H | H | H | H | H | N | CH | C=N—OC$_3$H$_7$-n |
| H | H | H | H | H | N—O$^-$ | CH | C=N—OC$_3$H$_7$-n |
| H | H | H | H | H | N | CH | C=N—OC$_3$H$_7$-iso |
| H | H | H | H | H | N | CH | C=N—OC$_4$H$_9$-n |
| H | H | H | H | H | N$^+$O$^-$ | CH | C=N—OC$_4$H$_9$-n |
| H | H | H | H | H | N | CH | C=N—OC$_4$H$_9$-iso |
| H | H | H | H | H | N$^+$—O$^-$ | CH | C=N—OC$_4$H$_9$-iso |
| H | H | H | H | H | N | CH | C=N—O—C$_5$H$_{11}$-n |
| H | H | H | H | H | N | CH | C=N—O—C$_6$H$_{13}$-n |

TABLE 1-continued

| $R^1$ | $R^2$ | $R^3$ | $R^4$ | $R^5$ | X | Y | Z |
|---|---|---|---|---|---|---|---|
| H | H | H | H | H | $N^+$—$O^-$ | CH | C=N—O—$C_6H_{13}$-n |
| H | H | H | H | H | N | CH | C=N—O—$CH_2$—CH=$CH_2$ |
| H | H | H | H | H | N | CH | C=N—O—$CH_2$—CH=CH—$CH_3$ |
| H | H | H | H | H | N | CH | C=N—O—$CH_2$—C(Cl)=$CH_2$ |
| H | H | H | H | H | $N^+$—$O^-$ | CH | C=N—O—$CH_2$—C(Cl)=$CH_2$ |
| H | H | H | H | H | N | CH | C=N—O—$CH_2$—C(Br)=$CH_2$ |
| H | H | H | H | H | N | CH | C=N—O—$CH_2$—CH=CH—Cl |
| H | H | H | H | H | N | CH | C=N—O—$CH_2$—CH=C($CH_3$)$_2$ |
| H | H | H | H | H | N | CH | C=N—O—$CH_2$—C($CH_3$)=CH—$CH_3$ |
| H | H | H | H | H | N | CH | C=N—O—$CH_2$—C($CH_3$)=$CH_2$ |
| H | H | H | H | H | N | CH | C=N—O—$CH_2$—C(Cl)=$CCl_2$ |
| H | H | H | H | H | N | CH | C=N—O—$CH_2$—$CH_2$—Cl |
| H | H | H | H | H | N | CH | C=N—O—$CH_2$—$CH_2$—$CH_2$Cl |
| H | H | H | H | H | N | CH | C=N—O—$CH_2$—$CH_2$—$CH_2$Br |
| H | H | H | H | H | N | CH | C=N—O—$(CH_2)_4$Cl |
| H | H | H | H | H | N | CH | C=N—O—$CH_2$—CHBr—$CH_2$Br |
| H | H | H | H | H | N | CH | C=N—O—$(CH_2)_6$Cl |
| H | H | H | H | H | N | CH | C=N—O—$(CH_2)_6$Br |
| H | H | H | H | H | N | CH | C=N—O—$CH_2$—$COOCH_3$ |
| H | H | H | H | H | N | CH | C=N—O—$CH_2$—$COOC_2H_5$ |
| H | H | H | H | H | N | CH | C=N—O—$CH_2$—$COOC_4H_9$-n |
| H | H | H | H | H | N | CH | C=N—O—$CH_2$—$COOC_4H_9$-tert |
| H | H | H | H | H | $N^+$—$O^-$ | CH | C=N—O—$CH_2$—$COOC_2H_5$ |
| H | H | H | H | H | N | CH | C=N—O—$CH_2$—C≡CH |
| H | H | H | H | H | N | CH | C=N—O—CH—C≡C—$CH_3$ |
| H | H | H | H | H | N | CH | C=N—O—$CH_2C_6H_5$ |
| H | H | H | H | H | $N^+$—$O^-$ | CH | C=N—$OCH_2C_6H_5$ |
| H | H | H | H | H | N | CH | C=N—O—$CH_2CH_2C_6H_5$ |
| H | H | H | H | H | N | CH | C=N—O—$(CH_2)_3C_6H_5$ |
| H | H | H | H | H | N | CH | C=N—$OCH_2$CH=CH—$C_6H_5$ |
| H | H | H | H | H | N | CH | C=N—$OCH_2$CH=CH—$CH_2$—$C_6H_5$ |
| H | H | H | H | H | N | CH | C=N—O—$CH_2CH_2$CH=CH—$C_6H_5$ |
| H | H | H | H | H | N | CH | C=N—O—$(CH_2)_5$—$C_6H_5$ |
| H | H | H | H | H | N | CH | C=N—$O(CH_2)_6$—$C_6H_5$ |
| H | H | H | H | H | N | CH | C=N—O—$CH_2$—CH($CH_3$)$CH_2C_6H_5$ |
| H | H | H | H | H | N | CH | C=N—O—$CH_2$—$C_6H_4$-4F |
| H | H | H | H | H | N | CH | C=N—O—$CH_2$—$C_6H_4$-2F |
| H | H | H | H | H | N | CH | C=N—O—$CH_2$—$C_6H_4$-2Cl |
| H | H | H | H | H | N | CH | C=N—O—$CH_2$—$C_6H_4$-4Cl |
| H | H | H | H | H | N | CH | C=N—O—$CH_2CH_2$—$C_6H_4$-2F |
| H | H | H | H | H | N | CH | C=N—O—$CH_2CH_2$—$C_6H_4$-4F |
| H | H | H | H | H | N | CH | C=N—O—$(CH_2)_3$—$C_6H_4$-4F |
| H | H | H | H | H | N | CH | C=N—O—$CH_2$—CH($CH_3$)$CH_2$—$C_6H_4$-4Cl |
| H | H | H | H | H | N | CH | C=N—O—$(CH_2)_4C_6H_4$-4Cl |
| H | H | H | H | H | N | CH | C=N—O—$CH_2$—CH=CH—$C_6H_4$-4Cl |
| H | H | H | H | H | N | CH | C=N—O—$CH_2$—CH=CH—$CH_2$—$C_6H_4$-4Cl |
| H | H | H | H | H | N | CH | C=N—O—$CH_2CH_2$CH=CH—$C_6H_4$-4Cl |
| H | H | H | H | H | N | CH | C=N—O—$CH_2$—$C_6H_4$-4$CH_3$ |
| H | H | H | H | H | N | CH | C=N—O—$CH_2$—$C_6H_4$-2$CH_3$ |
| H | H | H | H | H | N | CH | C=N—O—$CH_2$—$C_6H_4$-3$CF_3$ |
| H | H | H | H | H | N | CH | C=N—O—$CH_2$—$C_6H_4$-4$CF_3$ |
| H | H | H | H | H | N | CH | C=N—O—$CH_2$—$C_6H_4$-4$C_2H_5$ |
| H | H | H | H | H | N | CH | C=N—O—$CH_2$—$C_6H_4$-$C_4H_9$-tert |
| H | H | H | H | H | N | CH | C=N—O—$CH_2$—$C_6H_3$-3,4$Cl_2$ |
| H | H | H | H | H | N | CH | C=N—O—$CH_2$—$C_6H_3$-2,4$Cl_2$ |
| H | H | H | H | H | N | CH | C=N—$OCH_2$—$C_6H_4$-4$OCH_3$ |
| H | H | H | H | H | N | CH | C=N—$OCH_2$—$C_6H_4$-4$OC_2H_5$ |
| H | H | H | H | H | N | CH | C=N—$OCH_2$—$C_6H_4$-4$NO_2$ |
| H | H | H | H | H | N | CH | C=N—$OCH_2$—$C_6H_4$-4N($CH_3$)$_2$ |
| H | H | H | H | H | N | CH | C=N—$OCH_2$—$C_6H_4$-4N($C_2H_5$)$_2$ |
| H | H | H | H | H | N | CH | C=N—O—$CH_2$-2-thienyl |
| H | H | H | H | H | N | CH | C=N—O—$CH_2$-3-thienyl |
| H | H | H | H | H | N | CH | C=N—O—$CH_2CH_2$-2-thienyl |
| H | H | H | H | H | N | CH | C=N—O—$(CH_2)_3$-2-thienyl |
| H | H | H | H | H | N | CH | C=N—$O(CH_2)_4$-)-2-thienyl |
| H | H | H | H | H | N | CH | C=N—O—$CH_2$—CH=CH-2-thienyl |
| H | H | H | H | H | N | CH | C=N—O—$CH_2$—CH=CH—$CH_2$-2-thienyl |
| H | H | H | H | H | N | CH | C=N—O—$CH_2$—$CH_2$CH=CH-2-thienyl |
| H | H | H | H | H | N | CH | C=N—O—$CH_2$—CH($CH_3$)$CH_2$-2-thienyl |
| H | H | H | H | H | N | CH | C=$NOCH_2CH_2$-3-thienyl |
| H | H | H | H | H | N | CH | C=$NO(CH_2)_3$-3-thienyl |
| H | H | H | H | H | N | CH | C=$NO(CH_2)_4$-3-thienyl |
| H | H | H | H | H | N | CH | C=N—O—$CH_2$CH=CH-3-thienyl |
| H | H | H | H | H | N | CH | C=N—O—$CH_2$—CH=CH—$CH_2$-3-thienyl |
| H | H | H | H | H | N | CH | C=N—O—$CH_2CH_2$CH=CH-3-thienyl |
| H | H | H | H | H | N | CH | C=N—O—$CH_2$-(5-F-2-thienyl) |
| H | H | H | H | H | N | CH | C=N—O—$CH_2$-(4-F-2-thienyl) |

TABLE 1-continued

| R$^1$ | R$^2$ | R$^3$ | R$^4$ | R$^5$ | X | Y | Z |
|---|---|---|---|---|---|---|---|
| H | H | H | H | H | N | CH | C=N—OCH$_2$-(5Cl-2-thienyl) |
| H | H | H | H | H | N | CH | C=N—OCH$_2$-(5-Br-2-thienyl) |
| H | H | H | H | H | N | CH | C=N—O—CH$_2$(5-Cl-3-thienyl) |
| H | H | H | H | H | N | CH | C=N—O—CH$_2$-3-isoxazolyl |
| H | H | H | H | H | N | CH | C=N—O—CH$_2$-4-isoxazolyl |
| H | H | H | H | H | N | CH | C=N—O—CH$_2$-5-isoxazolyl |
| H | H | H | H | H | N | CH | C=N—NH—C$_6$H$_5$ |
| H | H | H | H | H | N | CH | C=N—NH—CH$_3$ |
| H | H | H | H | H | N | CH | C=N—N(CH$_3$)C$_6$H$_5$ |
| H | H | H | H | H | N | CH | C=N—NH—C$_6$H$_4$-4F |
| H | H | H | H | H | N | CH | C=N—NH—C$_6$H$_4$-4Cl |
| H | H | H | H | H | N | CH | C=N—NH—C$_6$H$_4$-4Br |
| H | H | H | H | H | N | CH | C=N—NH—C$_6$H$_4$-3CF$_3$ |
| H | H | H | H | H | N | CH | C=N—NH—C$_6$H$_4$-4CF$_3$ |
| H | H | H | H | H | N | CH | C=N—NH—C$_6$H$_4$-4OCH$_3$ |
| H | H | H | H | H | N | CH | C=N—NH—C$_6$H$_4$-4OC$_2$H$_5$ |
| H | H | H | H | H | N | CH | C=N—NH—C$_6$H$_4$-4NO$_2$ |
| H | H | H | H | H | N | CH | C=N—NH—C$_6$H$_4$-4CH$_3$ |
| H | H | H | H | H | N | CH | C=N—NH—C$_6$H$_4$-4C$_4$H$_9$-tert. |
| H | H | H | H | H | N | CH | C=N—NH—C$_6$H$_4$-N(CH$_3$)$_2$ |
| H | H | H | H | H | N | CH | C=H—NH—C$_6$H$_3$-2,4Cl$_2$ |
| H | H | H | H | H | N | CH | C=N—NH—C$_3$H$_7$-iso |
| H | H | H | H | H | CH | N | C=O |
| H | H | H | H | H | CH | N$^+$—O$^-$ | C=O |
| H | H | H | H | H | CH | N | CH—OH |
| H | H | H | H | H | CH | N | CH—OCH$_3$ |
| H | H | H | H | H | CH | N | CH—OC$_3$H$_7$-n |
| H | H | H | H | H | CH | N | CH—OCH$_2$—C$_6$H$_5$ |
| H | H | H | H | H | CH | N | CH—OCOCH$_3$ |
| H | H | H | H | H | CH | N | CH—OCOCH$_2$CH$_3$ |
| H | H | H | H | H | CH | N$^+$—O$^-$ | CH—OCOCH$_2$CH$_3$ |
| H | H | H | H | H | CH | N | CH—OCOC$_6$H$_5$ |
| H | H | H | H | H | CH | N | C=N—NH—CH$_3$ |
| CH$_3$ | H | H | H | H | N | CH | C=O |
| CH$_3$ | H | H | H | H | N$^+$—O$^-$ | CH | C=O |
| CH$_3$ | H | H | H | H | N | CH | CH—OH |
| CH$_3$ | H | H | H | H | N | CH | CH—OCH$_3$ |
| CH$_3$ | H | H | H | H | N | CH | CH—OC$_3$H$_7$-n |
| CH$_3$ | H | H | H | H | N | CH | CH—OCOCH$_3$ |
| CH$_3$ | H | H | H | H | N | CH | CH—OCOCH$_2$CH$_3$ |
| CH$_3$ | H | H | H | H | N | CH | CH—OCO—C$_6$H$_4$-3CF$_3$ |
| CH$_3$ | H | H | H | H | N | CH | C=N—OCH$_3$ |
| CH$_3$ | H | H | H | H | N | CH | C=N—N(CH$_3$)$_2$ |
| CH$_3$ | H | H | H | H | N | CH | C=N—NH—C$_6$H$_4$-4Cl |
| C$_2$H$_5$ | H | H | H | H | N | CH | C=O |
| C$_2$H$_5$ | H | H | H | H | N$^+$—O$^-$ | CH | C=O |
| C$_2$H$_5$ | H | H | H | H | N | CH | CH—OH |
| C$_2$H$_5$ | H | H | H | H | N | CH | CH—OC$_3$H$_7$-n |
| C$_2$H$_5$ | H | H | H | H | N | CH | CH—O—CH$_2$—C$_6$H$_4$-4Cl |
| C$_2$H$_5$ | H | H | H | H | N | CH | CH—OCOCH$_3$ |
| C$_2$H$_5$ | H | H | H | H | N | CH | CH—OCOCH$_2$CH$_3$ |
| C$_2$H$_5$ | H | H | H | H | N | CH | CH—OCOC$_6$H$_4$-4Cl |
| C$_2$H$_5$ | H | H | H | H | N | CH | C=N—OH |
| C$_2$H$_5$ | H | H | H | H | N | CH | C=N—NH—C$_3$H$_7$-iso |
| C$_2$H$_5$ | H | H | H | H | N | CH | C=N—NH—C$_6$H$_4$-3CF$_3$ |
| H | F | H | H | H | N | CH | C=O |
| H | F | H | H | H | N$^+$—O$^-$ | CH | C=O |
| H | F | H | H | H | N | CH | CH—OH |
| H | F | H | H | H | N | CH | CH—O—CH$_2$—C$_6$H$_4$-4F |
| H | F | H | H | H | N | CH | CH—OCOCH$_3$ |
| H | F | H | H | H | N | CH | CH—OCOCH$_2$CH$_3$ |
| H | F | H | H | H | N | CH | CH—OCOC$_6$H$_4$-4F |
| H | F | H | H | H | N | CH | CH—OCOC$_6$H$_4$-3CF$_3$ |
| H | F | H | H | H | N | CH | C=N—NH—CH$_3$ |
| H | F | H | H | H | N | CH | C=N—NH—C$_6$H$_4$-4NO$_2$ |
| H | H | F | H | H | N | CH | C=O |
| H | H | F | H | H | N$^+$—O$^-$ | CH | C=O |
| H | H | F | H | H | N | CH | CH—OH |
| H | H | F | H | H | N | CH | CH—OC$_3$H$_7$-n |
| H | H | F | H | H | N | CH | CH—OCOCH$_3$ |
| H | H | F | H | H | N | CH | CH—OCOCH$_2$CH$_3$ |
| H | H | F | H | H | N | CH | CH—OCOC$_6$H$_4$-4Cl |
| H | H | F | H | H | N | CH | CH—OCOC$_6$H$_4$-3CF$_3$ |
| H | H | F | H | H | N | CH | CH—OCOC$_6$H$_4$-4NO$_2$ |
| H | H | F | H | H | N | CH | C=N—OH |
| H | H | H | F | H | N | CH | C=O |
| H | H | H | F | H | N$^+$—O$^-$ | CH | C=O |

TABLE 1-continued

| R¹ | R² | R³ | R⁴ | R⁵ | X | Y | Z |
|---|---|---|---|---|---|---|---|
| H | H | H | F | H | N | CH | CH—OH |
| H | H | H | F | H | N | CH | CH—OCH₃ |
| H | H | H | F | H | N | CH | CH—OC₃H₇-n |
| H | H | H | F | H | N | CH | CH—OCOCH₃ |
| H | H | H | F | H | N | CH | CH—OCOCH₂CH₃ |
| H | H | H | F | H | N | CH | CH—OCO—C₆H₄-3CF₃ |
| H | H | H | F | H | N | CH | C=N—OCH₃ |
| H | H | H | F | H | N | CH | C=N—N(CH₃)₂ |
| H | H | H | F | H | N | CH | C=N—NH—C₆H₄-4Cl |
| H | H | H | H | F | N | CH | C=O |
| H | H | H | H | F | N⁺—O⁻ | CH | C=O |
| H | H | H | H | F | N | CH | CH—OH |
| H | H | H | H | F | N | CH | CH—OC₃H₇-n |
| H | H | H | H | F | N | CH | CH—O—CH₂—C₆H₄-4Cl |
| H | H | H | H | F | N | CH | CH—OCOCH₃ |
| H | H | H | H | F | N | CH | CH—OCOCH₂CH₃ |
| H | H | H | H | F | N | CH | CH—OCOC₆H₄-4Cl |
| H | H | H | H | F | N | CH | C=N—OH |
| H | H | H | H | F | N | CH | C=N—NH—C₃H₇-iso |
| H | H | H | H | H | N | CH | C=N—NH—C₆H₄-3CF₃ |
| H | Cl | H | H | H | N | CH | C=O |
| H | Cl | H | H | H | N⁺—O⁻ | CH | C=O |
| H | Cl | H | H | H | N | CH | CH—OH |
| H | Cl | H | H | H | N | CH | CH—OCOCH₃ |
| H | Cl | H | H | H | N⁺—O⁻ | CH | CH—OCOCH₃ |
| H | Cl | H | H | H | N | CH | CH—OCOCH₂CH₃ |
| H | Cl | H | H | H | N | CH | CH—OCOCH₂CH₂CH₃ |
| H | Cl | H | H | H | N | CH | CH—OCOC₆H₅ |
| H | Cl | H | H | H | N | CH | CH—OCOC₆H₄-3CF₃ |
| H | Cl | H | H | H | N | CH | C=N—N(CH₃)₂ |
| H | Cl | H | H | H | N | CH | C=N—NH—C₆H₅ |
| H | H | Cl | H | H | N | CH | C=O |
| H | H | Cl | H | H | N⁺—O⁻ | CH | C=O |
| H | H | Cl | H | H | N | CH | CH—OH |
| H | H | Cl | H | H | N | CH | CH—O—CH₂—C₆H₄-4F |
| H | H | Cl | H | H | N | CH | CH—OCOCH₃ |
| H | H | Cl | H | H | N | CH | CH—OCOCH₂CH₃ |
| H | H | Cl | H | H | N | CH | CH—OCOC₆H₄-4F |
| H | H | Cl | H | H | N | CH | CH—OCOC₆H₄-2-CF₃ |
| H | H | Cl | H | H | N | CH | C=N—NH—CH₃ |
| H | H | Cl | H | H | N | CH | C=N—NH—C₆H₄-4NO₂ |
| H | H | H | Cl | H | N | CH | C=O |
| H | H | H | Cl | H | N⁺—O⁻ | CH | C=O |
| H | H | H | Cl | H | N | CH | CH—OH |
| H | H | H | Cl | H | N | CH | CH—OC₃H₇-n |
| H | H | H | Cl | H | N | CH | CH—OCOCH₃ |
| H | H | H | Cl | H | N | CH | CH—OCOCH₂CH₃ |
| H | H | H | Cl | H | N | CH | CH—OCOC₆H₄-4Cl |
| H | H | H | Cl | H | N | CH | CH—OCOC₆H₄-3CH₃ |
| H | H | H | Cl | H | N | CH | CH—OCOC₆H₄-4NO₂ |
| H | H | H | Cl | H | N | CH | C=N—OH |
| H | H | H | H | Cl | N | CH | C=O |
| H | H | H | H | Cl | N⁺—O⁻ | CH | C=O |
| H | H | H | H | Cl | N | CH | CH—OH |
| H | H | H | H | Cl | N | CH | CH—OCH₃ |
| H | H | H | H | Cl | N | CH | CH—OC₃H₇-n |
| H | H | H | H | Cl | N | CH | CH—OCOCH₃ |
| H | H | H | H | Cl | N | CH | CH—OCOCH₂CH₃ |
| H | H | H | H | Cl | N | CH | CH—OCO—C₆H₄-3CF₃ |
| H | H | H | H | Cl | N | CH | C=N—OCH₃ |
| H | H | H | H | Cl | N | CH | C=N—N(CH₃)₂ |
| H | H | H | H | H | N | CH | C=N—NH—C₆H₄-4Cl |
| H | CH₃ | H | H | H | N | CH | C=O |
| H | CH₃ | H | H | H | N⁺—O⁻ | CH | C=O |
| H | CH₃ | H | H | H | N | CH | CH—OH |
| H | CH₃ | H | H | H | N | CH | CH—OC₃H₇-n |
| H | CH₃ | H | H | H | N | CH | CH—O—CH₂—C₆H₄-4Cl |
| H | CH₃ | H | H | H | N | CH | CH—OCOCH₃ |
| H | CH₃ | H | H | H | N | CH | CH—OCOCH₂CH₃ |
| H | CH₃ | H | H | H | N | CH | CH—OCOC₆H₄-4Cl |
| H | CH₃ | H | H | H | N | CH | C=N—OH |
| H | CH₃ | H | H | H | N | CH | C=N—NH—C₃H₇-iso |
| H | CH₃ | H | H | H | N | CH | C=N—NH—C₆H₄-3CF₃ |
| H | H | CH₃ | H | H | N | CH | C=O |
| H | H | CH₃ | H | H | N⁺—O⁻ | CH | C=O |
| H | H | CH₃ | H | H | N | CH | CH—OH |
| H | H | CH₃ | H | H | N | CH | CH—OCOCH₃ |

TABLE 1-continued

| R¹ | R² | R³ | R⁴ | R⁵ | X | Y | Z |
|---|---|---|---|---|---|---|---|
| H | H | CH₃ | H | H | N⁺—O⁻ | CH | CH—OCOCH₃ |
| H | H | CH₃ | H | H | N | CH | CH—OCOCH₂CH₃ |
| H | H | CH₃ | H | H | N | CH | CH—OCOCH₂CH₂CH₃ |
| H | H | CH₃ | H | H | N | CH | CH—OCOC₆H₅ |
| H | H | CH₃ | H | H | N | CH | CH—OCOC₆H₄-3CF₃ |
| H | H | CH₃ | H | H | N | CH | C=N—N(CH₃)₂ |
| H | H | CH₃ | H | H | N | CH | C=N—NH—C₆H₅ |
| H | H | H | CH₃ | H | N | CH | C=O |
| H | H | H | CH₃ | H | N⁺—O⁻ | CH | C=O |
| H | H | H | CH₃ | H | N | CH | CH—OH |
| H | H | H | CH₃ | H | N | CH | CH—O—CH₂—C₆H₄-4Cl |
| H | H | H | CH₃ | H | N | CH | CH—OCOCH₃ |
| H | H | H | CH₃ | H | N | CH | CH—OCOCH₂CH₂CH₃ |
| H | H | H | CH₃ | H | N | CH | CH—OCOC₆H₄-4F |
| H | H | H | CH₃ | H | N | CH | CH—OCOC₆H₄-3CF₃ |
| H | H | H | CH₃ | H | N | CH | C=N—NH—CH₃ |
| H | H | H | CH₃ | H | N | CH | C=N—NH—C₆H₄-4NO₂ |
| H | H | H | H | CH₃ | N | CH | C=O |
| H | H | H | H | CH₃ | N⁺—O⁻ | CH | C=O |
| H | H | H | H | CH₃ | N | CH | CH—OH |
| H | H | H | H | CH₃ | N | CH | CH—OC₃H₇-n |
| H | H | H | H | CH₃ | N | CH | CH—OCOCH₃ |
| H | H | H | H | CH₃ | N | CH | CH—OCOCH₂CH₃ |
| H | H | H | H | CH₃ | N | CH | CH—OCOC₆H₄-4Cl |
| H | H | H | H | CH₃ | N | CH | CH—OCOC₆H₄-3CF₃ |
| H | H | H | H | CH₃ | N | CH | CH—OCOC₆H₄-4NO₂ |
| H | H | H | H | CH₃ | N | CH | C=N—OH |
| H | C₃H₇-iso | H | H | H | N | CH | C=O |
| H | C₃H₇-iso | H | H | H | N⁺—O⁻ | CH | C=O |
| H | C₃H₇-iso | H | H | H | N | CH | CH—OH |
| H | C₃H₇-iso | H | H | H | N | CH | CH—OCH₃ |
| H | C₃H₇-iso | H | H | H | N | CH | CH—OC₃H₇-n |
| H | C₃H₇-iso | H | H | H | N | CH | CH—OCOCH₃ |
| H | C₃H₇-iso | H | H | H | N | CH | CH—OCOCH₂CH₃ |
| H | C₃H₇-iso | H | H | H | N | CH | CH—OCO—C₆H₄-3CF₃ |
| H | C₃H₇-iso | H | H | H | N | CH | C=N—OCH₃ |
| H | C₃H₇-iso | H | H | H | N | CH | C=N—N(CH₃)₂ |
| H | C₃H₇-iso | H | H | H | N | CH | C=N—NH—C₆H₄-4Cl |
| H | H | C₃H₇-iso | H | H | N | CH | C=O |
| H | H | C₃H₇-iso | H | H | N⁺—O⁻ | CH | C=O |
| H | H | C₃H₇-iso | H | H | N | CH | CH—OH |
| H | H | C₃H₇-iso | H | H | N | CH | CH—OC₃H₇-n |
| H | H | C₃H₇-iso | H | H | N | CH | CH—O—CH₂—C₆H₄-4Cl |
| H | H | C₃H₇-iso | H | H | N | CH | CH—OCOCH₃ |
| H | H | C₃H₇-iso | H | H | N | CH | CH—OCOCH₂CH₃ |
| H | H | C₃H₇-iso | H | H | N | CH | CH—OCOC₆H₄-4Cl |
| H | H | C₃H₇-iso | H | H | N | CH | C=N—OH |
| H | H | C₃H₇-iso | H | H | N | CH | C=N—NH—C₃H₇-iso |
| H | H | C₃H₇-iso | H | H | N | CH | C=N—NH—C₆H₄-3CF₃ |
| H | H | H | C₃H₇-iso | H | N | CH | C=O |
| H | H | H | C₃H₇-iso | H | N⁺—O⁻ | CH | C=O |
| H | H | H | C₃H₇-iso | H | N | CH | CH—OH |
| H | H | H | C₃H₇-iso | H | N | CH | CH—OCOCH₃ |
| H | H | H | C₃H₇-iso | H | N⁺—O⁻ | CH | CH—OCOCH₃ |
| H | H | H | C₃H₇-iso | H | N | CH | CH—OCOCH₂CH₃ |
| H | H | H | C₃H₇-iso | H | N | CH | CH—OCOCH₂CH₂CH₃ |
| H | H | H | C₃H₇-iso | H | N | CH | CH—OCOC₆H₅ |
| H | H | H | C₃H₇-iso | H | N | CH | CH—OCOC₆H₄-3CF₃ |
| H | H | H | C₃H₇-iso | H | N | CH | C=N—N(CH₃)₂ |
| H | H | H | C₃H₇-iso | H | N | CH | C=N—NH—C₆H₅ |
| H | H | H | C₄H₉-iso | H | N | CH | C=O |
| H | H | C₄H₉-iso | H | H | N⁺—O⁻ | CH | C=O |
| H | H | C₄H₉-iso | H | H | N | CH | CH—OH |
| H | H | C₄H₉-iso | H | H | N | CH | CH—OCOCH₃ |
| H | H | C₄H₉-iso | H | H | N | CH | CH—O—CH₂—C₆H₄-4Cl |
| H | H | C₄H₉-iso | H | H | N | CH | CH—OCOCH₃ |
| H | H | C₄H₉-iso | H | H | N | CH | CH—OCOCH₂CH₂CH₃ |
| H | H | C₄H₉-iso | H | H | N | CH | CH—OCOC₆H₄-4F |
| H | H | C₄H₉-iso | H | H | N | CH | CH—OCOC₆H₄-3CF₃ |
| H | H | C₄H₉-iso | H | H | N | CH | C=N—NH—CH₃ |
| H | H | C₄H₉-iso | H | H | N | CH | C=N—NH—C₆H₄-4NO₂ |
| H | H | H | C₄H₉-iso | H | N | CH | C=O |
| H | H | H | C₄H₉-iso | H | N⁺—O⁻ | CH | C=O |
| H | H | H | C₄H₉-iso | H | N | CH | C=O |
| H | H | H | C₄H₉-iso | H | N | CH | CH—OH |
| H | H | H | C₄H₉-iso | H | N | CH | CH—OC₃H₇-n |
| H | H | H | C₄H₉-iso | H | N | CH | CH—OCOCH₃ |
| H | H | H | C₄H₉-iso | H | N | CH | CH—OCOC₆H₄-4Cl |

TABLE 1-continued

| R¹ | R² | R³ | R⁴ | R⁵ | X | Y | Z |
|---|---|---|---|---|---|---|---|
| H | H | H | C₄H₉-iso | H | N | CH | CH—OCOC₆H₄-3CF₃ |
| H | H | H | C₄H₉-iso | H | N | CH | CH—OCOC₆H₄-4NO₂ |
| H | H | H | C₄H₉-iso | H | N | CH | C=N—OH |
| H | H | C(CH₃)₃ | H | H | N | CH | C=O |
| H | H | C(CH₃)₃ | H | H | N⁺—O⁻ | CH | C=O |
| H | H | C(CH₃)₃ | H | H | N | CH | CH—OH |
| H | H | C(CH₃)₃ | H | H | N | CH | CH—OCH₃ |
| H | H | C(CH₃)₃ | H | H | N | CH | CH—OC₃H₇-n |
| H | H | C(CH₃)₃ | H | H | N | CH | CH—OCOCH₃ |
| H | H | C(CH₃)₃ | H | H | N | CH | CH—OCOCH₂CH₃ |
| H | H | C(CH₃)₃ | H | H | N | CH | CH—OCO—C₆H₄-3CF₃ |
| H | H | C(CH₃)₃ | H | H | N | CH | C=N—OCH₃ |
| H | H | C(CH₃)₃ | H | H | N | CH | C=N—N(CH₃)₂ |
| H | H | C(CH₃)₃ | H | H | N | CH | C=N—NH—C₆H₄-4Cl |
| H | H | H | C(CH₃)₃ | H | N | CH | C=O |
| H | H | H | C(CH₃)₃ | H | N⁺—O⁻ | CH | C=O |
| H | H | H | C(CH₃)₃ | H | N | CH | CH—OH |
| H | H | H | C(CH₃)₃ | H | N | CH | CH-OC₃H₇-n |
| H | H | H | C(CH₃)₃ | H | N | CH | CH—O—CH₂—C₆H₄-4Cl |
| H | H | H | C(CH₃)₃ | H | N | CH | CH—OCOCH₃ |
| H | H | H | C(CH₃)₃ | H | N | CH | CH—OCOCH₂CH₃ |
| H | H | H | C(CH₃)₃ | H | N | CH | CH—OCOC₆H₄-4Cl |
| H | H | H | C(CH₃)₃ | H | N | CH | C=N—OH |
| H | H | H | C(CH₃)₃ | H | N | CH | C=N—NH—C₃H₇-iso |
| H | H | H | C(CH₃)₃ | H | N | CH | C=N—NH—C₆H₄-3CF₃ |
| H | H | C₅H₁₁-iso | H | H | N | CH | C=O |
| H | H | C₅H₁₁-iso | H | H | N⁺—O⁻ | CH | C=O |
| H | H | C₅H₁₁-iso | H | H | N | CH | CH—OH |
| H | H | C₅H₁₁-iso | H | H | N | CH | CH—OCOCH₃ |
| H | H | C₅H₁₁-iso | H | H | N⁺—O⁻ | CH | CH—OCOCH₃ |
| H | H | C₅H₁₁-iso | H | H | N | CH | CH—OCOCH₂CH₃ |
| H | H | C₅H₁₁-iso | H | H | N | CH | CH—OCOCH₂CH₂CH₃ |
| H | H | C₅H₁₁-iso | H | H | N | CH | CH—OCOC₆H₅ |
| H | H | C₅H₁₁-iso | H | H | N | CH | CH—OCOC₆H₄-3CF₃ |
| H | H | C₅H₁₁-iso | H | H | N | CH | C=N—N(CH₃)₂ |
| H | H | C₅H₁₁-iso | H | H | N | CH | C=N—NH—C₆H₅ |
| H | H | C₆H₁₃-n | H | H | N | CH | C=O |
| H | H | C₆H₁₃-n | H | H | N⁺—O⁻ | CH | C=O |
| H | H | C₆H₁₃-n | H | H | N | CH | CH—OH |
| H | H | C₆H₁₃-n | H | H | N | CH | CH—OCH₂—C₆H₄-4Cl |
| H | H | C₆H₁₃-n | H | H | N | CH | CH—OCOCH₃ |
| H | H | C₆H₁₃-n | H | H | N | CH | CH—OCOCH₂CH₃ |
| H | H | C₆H₁₃-n | H | H | N | CH | CH—OCOC₆H₄-4F |
| H | H | C₆H₁₃-n | H | H | N | CH | CH—OCOC₆H₄-3CF₃ |
| H | H | C₆H₁₃-n | H | H | N | CH | C=N—NH—CH₃ |
| H | H | C₆H₁₃-n | H | H | N | CH | C=N—NH—C₆H₄-4NO₂ |
| H | OCH₃ | H | H | H | N | CH | C=O |
| H | OCH₃ | H | H | H | N⁺—O⁻ | CH | C=O |
| H | OCH₃ | H | H | H | N | CH | CH—OH |
| H | OCH₃ | H | H | H | N | CH | CH—OC₃H₇-n |
| H | OCH₃ | H | H | H | N | CH | CH—OCOCH₃ |
| H | OCH₃ | H | H | H | N | CH | CH—OCOCH₂CH₃ |
| H | OCH₃ | H | H | H | N | CH | CH—OCOC₆H₄-4Cl |
| H | OCH₃ | H | H | H | N | CH | CH—OCOC₆H₄-3CF₃ |
| H | OCH₃ | H | H | H | N | CH | CH—OCOC₆H₄-4NO₂ |
| H | OCH₃ | H | H | H | N | CH | C=N—OH |
| H | H | OCH₃ | H | H | N | CH | C=O |
| H | H | OCH₃ | H | H | N⁺—O⁻ | CH | C=O |
| H | H | OCH₃ | H | H | N | CH | CH—OH |
| H | H | OCH₃ | H | H | N | CH | CH—OCH₃ |
| H | H | OCH₃ | H | H | N | CH | CH—OC₃H₇-n |
| H | H | OCH₃ | H | H | N | CH | CH—OCOCH₃ |
| H | H | OCH₃ | H | H | N | CH | CH—OCOCH₂CH₃ |
| H | H | OCH₃ | H | H | N | CH | CH—OCO—C₆H₄-3CF₃ |
| H | H | OCH₃ | H | H | N | CH | C=N—OCH₃ |
| H | H | OCH₃ | H | H | N | CH | C=N—N(CH₃)₂ |
| H | H | OCH₃ | H | H | N | CH | C=N—NH—C₆H₄-4Cl |
| H | H | H | OCH₃ | H | N | CH | C=O |
| H | H | H | OCH₃ | H | N⁺—O⁻ | CH | C=O |
| H | H | H | OCH₃ | H | N | CH | CH—OH |
| H | H | H | OCH₃ | H | N | CH | CH—OC₃H₇-n |
| H | H | H | OCH₃ | H | N | CH | CH—O—CH₂—C₆H₄-4Cl |
| H | H | H | OCH₃ | H | N | CH | CH—OCOCH₃ |
| H | H | H | OCH₃ | H | N | CH | CH—OCOCH₂CH₃ |
| H | H | H | OCH₃ | H | N | CH | CH—OCOC₆H₄-4Cl |
| H | H | H | OCH₃ | H | N | CH | C=N—OH |
| H | H | H | OCH₃ | H | N | CH | C=N—NH—C₃H₇-iso |

TABLE 1-continued

| R¹ | R² | R³ | R⁴ | R⁵ | X | Y | Z |
|---|---|---|---|---|---|---|---|
| H | H | H | OCH₃ | H | N | CH | C=N—NH—C₆H₄-3CF₃ |
| H | H | H | OC₂H₅ | H | N | CH | C=O |
| H | H | H | OC₂H₅ | H | N⁺—O⁻ | CH | C=O |
| H | H | H | OC₂H₅ | H | N | CH | CH—OH |
| H | H | H | OC₂H₅ | H | N | CH | CH—OCOCH₃ |
| H | H | H | OC₂H₅ | H | N⁺—O⁻ | CH | CH—OCOCH₃ |
| H | H | H | OC₂H₅ | H | N | CH | CH—OCOCH₂CH₃ |
| H | H | H | OC₂H₅ | H | N | CH | CH—OCOCH₂CH₂CH₃ |
| H | H | H | OC₂H₅ | H | N | CH | CH—OCOC₆H₅ |
| H | H | H | OC₂H₅ | H | N | CH | CH—OCOC₆H₄-3CF₃ |
| H | H | H | OC₂H₅ | H | N | CH | C=N—N(CH₃)₂ |
| H | H | H | OC₂H₅ | H | N | CH | C=N—NH—C₆H₅ |
| H | H | H | OC₄H₉ | H | N | CH | C=O |
| H | H | H | OC₄H₉ | H | N⁺—O⁻ | CH | C=O |
| H | H | H | OC₄H₉ | H | N | CH | CH—OH |
| H | H | H | OC₄H₉ | H | N | CH | CH—O—CH₂—C₆H₄-4Cl |
| H | H | H | OC₄H₉ | H | N | CH | CH—OCOCH₃ |
| H | H | H | OC₄H₉ | H | N | CH | CH—OCOCH₂CH₃ |
| H | H | H | OC₄H₉ | H | N | CH | CH—OCOC₆H₄-4F |
| H | H | H | OC₄H₉ | H | N | CH | CH—OCOC₆H₄-3CF₃ |
| H | H | H | OC₄H₉ | H | N | CH | C=N—NH—CH₃ |
| H | H | H | OC₄H₉ | H | N | CH | C=N—NH—C₆H₄-4NO₂ |
| H | H | H | NO₂ | H | N | CH | C=O |
| H | H | H | NO₂ | H | N⁺—O⁻ | CH | C=O |
| H | H | H | NO₂ | H | N | CH | CH—OH |
| H | H | H | NO₂ | H | N | CH | CH—OC₃H₇-n |
| H | H | H | NO₂ | H | N | CH | CH—OCOCH₃ |
| H | H | H | NO₂ | H | N | CH | CH—OCOCH₂CH₃ |
| H | H | H | NO₂ | H | N | CH | CH—OCOC₆H₄-4Cl |
| H | H | H | NO₂ | H | N | CH | CH—OCOC₆H₄-3CF₃ |
| H | H | H | NO₂ | H | N | CH | CH—OCOC₆H₄-4NO₂ |
| H | H | H | NO₂ | H | N | CH | C=N—OH |
| H | Br | H | H | H | N | CH | C=O |
| H | Br | H | H | H | N | CH | CHOH |
| H | H | Br | H | H | N | CH | C=O |
| H | H | Br | H | H | N | CH | CHOH |
| H | H | H | Br | H | N | CH | C=O |
| H | H | H | Br | H | N | CH | CHOH |
| H | NO₂ | H | H | H | N | CH | C=O |
| H | NO₂ | H | H | H | N | CH | CHOH |
| H | H | H | NO₂ | H | N | CH | C=O |
| H | H | H | H | NO₂ | N | CH | C=O |
| H | COOC₂H₅ | H | H | H | N | CH | C=O |
| H | COOC₂H₅ | H | H | H | N | CH | CHOH |
| H | H | COOC₂H₅ | H | H | N | CH | C=O |
| H | H | COOC₂H₅ | H | H | N | CH | CHOH |
| H | CF₃ | H | H | H | N | CH | C=O |
| H | CF₃ | H | H | H | N | CH | CHOH |
| H | H | CF₃ | H | H | N | CH | C=O |
| H | H | CF₃ | H | H | N | CH | CHOH |
| H | H | H | CF₃ | H | N | CH | C=O |
| H | H | H | CF₃ | H | N | CH | CH—OH |
| H | CH₃ | CH₃ | H | H | N | CH | C=O |
| H | CH₃ | CH₃ | H | H | N | CH | CH—OH |
| H | CH₃ | H | CH₃ | H | N | CH | C=O |
| H | CH₃ | H | CH₃ | H | N | CH | CHOH |
| H | H | CH₃ | CH₃ | H | N | CH | C=O |
| H | H | CH₃ | CH₃ | H | N | CH | CH—OH |
| H | H | CH₃ | H | F | N | CH | CH—OH |
| H | H | CH₃ | H | F | N | CH | C=O |
| H | H | CH₃ | Cl | H | N | CH | C=O |
| H | H | CH₃ | Cl | H | N | CH | CHOH |
| H | H | C₃H₇-iso | H | F | N | CH | C=O |
| H | H | C₃H₇-iso | H | F | N | CH | CH—OH |
| H | H | C(CH₃)₃ | H | F | N | CH | C=O |
| H | H | C(CH₃)₃ | H | F | N | CH | CHOH |
| H | F | F | H | H | N | CH | C=O |
| H | F | F | H | H | N | CH | CHOH |
| H | F | H | F | H | N | CH | C=O |
| H | F | H | F | H | N | CH | CH—OH |
| H | F | H | H | F | N | CH | C=O |
| H | F | H | H | F | N | CH | CH—OH |
| H | H | F | F | H | N | CH | C=O |
| H | H | F | F | H | N | CH | CH—OH |
| H | H | F | H | F | N | CH | C=O |
| H | H | F | H | F | N | CH | CH—OH |
| H | Cl | Cl | H | H | N | CH | C=O |

TABLE 1-continued

| $R^1$ | $R^2$ | $R^3$ | $R^4$ | $R^5$ | X | Y | Z |
|---|---|---|---|---|---|---|---|
| H | Cl | Cl | H | H | N | CH | CHOH |
| H | Cl | H | Cl | H | N | CH | C=O |
| H | Cl | H | Cl | H | N | CH | CHOH |
| H | H | Cl | Cl | H | N | CH | CHOH |
| H | H | Cl | Cl | H | N | CH | C=O |
| H | F | Cl | H | H | N | CH | C=O |
| H | F | Cl | H | H | N | CH | CHOH |
| H | H | Cl | H | F | N | CH | C=O |
| H | H | Cl | H | F | N | CH | CHOH |
| H | OCH$_3$ | OCH$_3$ | H | H | N | CH | C=O |
| H | OCH$_3$ | OCH$_3$ | H | H | N | CH | CHOH |
| H | OCH$_3$ | OCH$_3$ | H | F | N | CH | C=O |
| H | OCH$_3$ | OCH$_3$ | H | F | N | CH | CHOH |
| H | OCH$_3$ | H | OCH$_3$ | H | N | CH | C=O |
| H | OCH$_3$ | H | OCH$_3$ | H | N | CH | CHOH |
| H | H | OCH$_3$ | OCH$_3$ | H | N | CH | CHOH |
| H | H | OCH$_3$ | OCH$_3$ | H | N | CH | C=O |
| H | H | Cl | OCH$_3$ | H | N | CH | C=O |
| H | H | Cl | OCH$_3$ | H | N | CH | CHOH |
| H | H | OCH$_3$ | H | F | N | CH | C=O |
| H | H | OCH$_3$ | H | F | N | CH | CHOH |
| H | CH$_3$ | OCH$_3$ | H | H | N | CH | CHOH |
| H | CH$_3$ | OCH$_3$ | H | H | N | CH | C=O |
| H | H | CH$_3$ | OCH$_3$ | H | N | CH | C=O |
| H | H | CH$_3$ | OCH$_3$ | H | N | CH | CHOH |
| H | H | Br | OCH$_3$ | H | N | CH | C=O |
| H | H | Br | OCH$_3$ | H | N | CH | CHOH |
| H | NO$_2$ | H | OCH$_3$ | H | N | CH | C=O |
| H | NO$_2$ | H | OCH$_3$ | H | N | CH | CH—OH |
| H | H | NO$_2$ | OCH$_3$ | H | N | CH | C=O |
| H | H | NO$_2$ | OCH$_3$ | H | N | CH | CHOH |
| H | OCH$_3$ | Cl | OCH$_3$ | H | N | CH | C=O |
| H | OCH$_3$ | Cl | OCH$_3$ | H | N | CH | CHOH |
| H | H | C(CH$_3$)$_3$ | OCH$_3$ | H | N | CH | C=O |
| H | H | C(CH$_3$)$_3$ | OCH$_3$ | H | N | CH | CHOH |
| H | H | OC$_2$H$_5$ | OC$_2$H$_5$ | H | N | CH | C=O |
| H | H | OC$_2$H$_5$ | OC$_2$H$_5$ | H | N | CH | CHOH |
| H | H | Cl | OC$_2$H$_5$ | H | N | CH | C=O |
| H | H | Cl | OC$_2$H$_5$ | H | N | CH | CHOH |
| H | CH$_3$ | CH$_3$ | CH$_3$ | H | N | CH | C=O |
| H | CH$_3$ | CH$_3$ | CH$_3$ | H | N | CH | CHOH |
| H | OCH$_3$ | OCH$_3$ | CH$_3$O | H | N | CH | C=O |
| H | OCH$_3$ | OCH$_3$ | OCH$_3$ | H | N | CH | CHOH |
| H | OCH$_3$ | OCH$_3$ | OCH$_3$ | F | N | CH | C=O |
| H | OCH$_3$ | OCH$_3$ | OCH$_3$ | F | N | CH | CHOH |
| H | H | F | OCH$_3$ | F | N | CH | C=O |
| H | H | F | OCH$_3$ | F | N | CH | CHOH |
| H | H | CF$_3$ | OCH$_3$ | H | N | CH | C=O |
| H | H | CF$_3$ | OCH$_3$ | H | N | CH | CHOH |
| H | H | CF$_3$ | CH$_3$ | H | N | CH | CHOH |
| H | H | CF$_3$ | CH$_3$ | H | N | CH | C=O |

The compounds I and Ia and the herbicidal compositions containing them and their environmentally tolerable salts can highly effectively control broad-leaved weeds and grass weeds in crops such as wheat, rice, maize, soybeans and cotton without harming the crop plants, an effect which occurs especially even at low application rates.

The compounds I and Ia and the herbicidal compositions containing them can be applied by spraying, atomizing, dusting, scattering or watering, for example in the form of directly sprayable solutions, powders, suspensions, even high-percentage aqueous, oily or other suspensions, or dispersions, emulsions, oil dispersions, pastes, dusting compositions, scattering compositions or granules. The application forms depend on the intended uses; in each case they should if possible ensure the finest dispersion of the active compounds according to the invention.

The compounds I and Ia are generally suitable for the production of directly sprayable solutions, emulsions, pastes or oil dispersions. Suitable inert additives are mineral oil fractions of medium to high boiling points, such as kerosene or diesel oil, further coal tar oils and oils of vegetable or animal origin, aliphatic, cyclic and aromatic hydrocarbons, eg. toluene, xylene, paraffin, tetrahydronaphthalene, alkylated naphthalenes or their derivatives, alkylated benzenes or their derivatives, methanol, ethanol, propanol, butanol, cyclohexanol, cyclohexanone, chlorobenzene or strongly polar solvents, such as N-methylpyrrolidone or water.

Aqueous application forms can be prepared from emulsion concentrates, dispersions, pastes, wettable powders or water-dispersable granules by addition of water. To prepare emulsions, pastes or oil dispersions, the substrates can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Suitable surface-active substances are the alkali metal, alkaline earth metal or ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl-, lauryl ether and fatty alcohol sulfates, as well as salts of sulfated hexa-, hepta- and octadecanols, and also of fatty alcohol glycol ether, condensation products of sulfonated naphthalene and its derivatives with formaldehyde, condensation products of naphthalene or of the naphthalenesulfonic acids with phenol and formaldehyde, polyoxyethylene octylphenol ethers, ethoxylated isooctyl-, octyl- or nonylphenol, alkylphenol or tributylphenyl polyglycol ethers, alkylaryl polyether alcohols, isotridecyl alcohol, fatty alcoholethylene oxide condensates, ethoxylated castor oil, polyoxyethylene or polyoxypropylenealkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, eg. coated, impregnated and homogeneous granules, can be prepared by binding of the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic mate-rials, fertilizers, such as ammonium sulfate, ammonium phosphate, ammonium nitrate, ureas and vegetable products, such as grain flour, tree bark, wood and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably 95% to 100% (according to NMR spectrum/HPLC/GC).

Examples of such preparations are:

I. 20 parts by weight of the compound No. 50 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium dodecylbenzenesulfonate and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 50 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 50 are dissolved in a mixture which consists of 25 parts by weight of cyclohexanone, 65 parts by weight of a mineral oil fraction and boiling point from 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 50 are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. 50 are mixed with 97 parts by weight of finely divided kaolin. In this manner, a dusting composition is obtained which contains 3% by weight of the active compound.

VI. 20 parts by weight of the active compound No. 50 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the aim of control, time of year, target plants and stage of growth, the application rates of active compound are from 0.001 to 5.0, preferably from 0.01 to 2.0, kg/ha of active substance (a.s.).

In consideration of the versatility of the application methods, the compounds I and Ia according to the invention or compositions containing them can additionally be employed in a further number of crop plants for the elimination of undesired plants. Suitable crops, for example, are the following:

*Allium cepa, Ananas comosus, Arachis hypogaea, Asparagus officinalis, Beta vulgaris* spp., altissima, *Beta vulgaris* spp. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum* (*Gossypium arboreum, Gossypium herbaceum, Gossypium vitifolium*), *Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum* (*N. rustica*), *Olea europaea, Oryza sativa, Phaseolus lunatus, Phaseolus mungo, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

The growth-regulating active compounds I and Ia can differently affect virtually all stages of development of a plant. The variety of action of the plant growth regulators depends especially a) on the plant species and variety, b) on the time of application, relative to the stage of development of the plant, and on the time of year, c) on the type and process of application (eg. seed dressing, soil treatment, foliar application or trunk injection in the case of trees), d) on climatic factors, eg. temperature, amount of precipitation, and additionally length of day and light intensity, e) on the soil condition (including fertilization), f) on the formulation and application form of the active compound and finally g) on the concentration of the active substance applied.

From the number of different application possibilities of plant growth regulators of the formula I or Ia in plant cultivation, in agriculture and in horticulture, a few are mentioned below.

A. The vegetative growth of the plants can be strongly inhibited by the compounds utilizable according to the invention, which is manifested in particular in a reduction in the longitudinal growth.

The treated plants therefore have a stocky growth; additionally a darker leaf coloration is to be observed.

A decreased intensity in the growth of grasses and crops susceptible to lodging such as grain, maize, sunflowers and soybeans proves advantageous in practice. The culm shortening and culm strengthening caused in this case decrease or eliminate the danger of lodging (of being bent over) of plants under unfavorable weather conditions before harvesting.

The application of growth regulators for inhibiting the longitudinal growth and for temporally altering the course of ripening in cotton is also important. Completely mechanized harvesting of this important crop plant is thus made possible.

In the case of fruit and other trees, pruning costs can be saved using the growth regulators. In addition, the alternation of fruit trees can be broken by means of growth regulators.

The lateral branching of the plants can also be increased or inhibited by application of growth regulators. There is interest in this if, eg. in the case of tobacco plants, the formation of side shoots (suckers) is to be inhibited in favor of leaf growth.

In the case of winter rape, for example, the frost resistance can also be considerably increased using growth regulators. In this case, on the one hand, the longitudinal growth and the development of an excessively luxuriant (and thereby particularly frost-susceptible) herbage or biomass are inhibited. On the other hand, after sowing and before the winter frosts set in the young rape plants are held back in the vegetative development stage despite favorable growth conditions. As a result, the frost danger to those plants which are prone to premature degeneration of the inhibition of flowering and to transition into the generative phase is also eliminated. Even in other crops, eg. winter grain, it is advantageous if the populations are indeed well tillered by treatment with the compounds according to the invention in the fall, but are not too luxuriant when going into the winter. As a result, the increased frost sensitivity and, because of the relatively low herbage or biomass, attack by various diseases (eg. fungal disease) can be prevented.

B. Additional yields of parts of plants and of plant constituents can be achieved using the growth regulators. Thus it is possible, for example, to induce the growth of greater amounts of buds, flowers, leaves, fruits, seeds, roots and tubers, to increase the content of sugar in sugar beet, sugar cane and citrus fruits, to raise the protein content in grain or soybeans or to stimulate rubber trees to an increased flow of latex.

In this case, the compounds of the formula I or Ia can cause increases in yield by intervention in the plant metabolism or by promotion or inhibition of vegetative and/or of generative growth.

C. Finally, both reduction or prolongation of the development stages and acceleration or retardation of the ripening of the harvested parts of plants before or after harvesting can be achieved using plant growth regulators.

Of economic interest, for example, is the facilitation of harvesting, which is made possible by the temporally concentrated fall or decrease in the adhesiveness to the tree in the case of citrus fruits, olives or in the case of other species and varieties of pomes, drupes and indehiscent fruit. The same mechanism, ie. the promotion of the formation of abscission tissue between the fruit or leaf and shoot part of the plant is also essential for a well-controllable defo-liation of productive plants, such as, for example, cotton.

D. The water consumption of plants can furthermore be reduced using growth regulators. The intensity of irrigation can be reduced by the use of the substances according to the invention and thus a more economical management can be carried out, since, inter alia, the opening width of the stomata is reduced, a thicker epidermis and cuticle are formed, the root penetration of the soil is improved and the microclimate in the plant population is favorably affected by a more compact growth.

The compounds I and Ia are particularly suitable for culm shortening of crop plants such as barley, rape and wheat.

The active compounds of the formula I or Ia to be used according to the invention can be supplied to the crop plants both from seeds (as seed dressing agents) and via the soil, ie. by the roots and, particularly preferably, by spraying over the leaves.

As a result of the high plant compatibility, the application rate of active compound is not critical. The optimum application rate varies depending on the target of control, time of year, target plants and stages of growth.

In the treatment of seed, amounts of active compound of from 0.001 to 50 g, preferably from 0.01 to 10 g, are in general required per kilogram of seed.

For foliar and soil treatment, additions of from 0.001 to 10 kg/ha, in particular from 0.01 to 3 kg/ha, are in general to be considered as adequate.

To widen the spectrum of action and to achieve synergistic effects, the compounds of the general formula I or Ia can be mixed and applied together with numerous representatives of other herbicidal or growth-regulating active compound groups. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolinones, sulfonamides, sulfonylureas, aryloxy- or heteroaryloxyphenoxypropionic acids and their salts, esters and amides and others.

Additionally, it may useful to apply the compounds I and Ia on their own or in combination with other herbicides additionally mixed with further crop protection agents, for example with agents for controlling pests or phytopathogenic fungi or bacteria. Further of interest is the miscibility with mineral salt solutions, which are employed for the elimination of nutritional and trace element deficiencies. Nonphytotoxic oils and oil concentrates can also be added.

The preparation and the use of the active compounds I and Ia can be seen from the following examples.

PREPARATION EXAMPLES

EXAMPLE 1 a) 4-Methyl-5H-indeno[3,2-b]pyridin-5-one

A mixture of 51 g (0.211 mol) of ethyl 2-phenyl-4-methylnicotinate and 500 g of polyphosphoric acid was stirred at 140° C. for 7 hours, cooled, stirred into 700 g of ice, rendered alkaline with conc. ammonia solution and extracted with ethyl acetate. The combined extracts were washed twice with water, dried over $K_2CO_3$ and concentrated. The product thus obtained was then digested with diethyl ether for 2 hours, filtered off with suction and dried. Yield 18.6 g (45% of theory), yellowish crystals of m.p. 137°–139° C.

b) Ethyl 2-phenyl-4-methylnicotinate

In succession at 25° C. and with introduction of nitrogen, 192 g (1 mol) of ethyl benzoyl acetate in 20 min and a solution of 84 g (1.2 mol) of crotonaldehyde in 100 ml of dioxane were added dropwise with stirring in the course of 30 min to a suspension of 2 g of sodium hydride in dioxane. After stirring for 10 hours, the reaction mixture was treated with 800 ml of acetic acid and then with 245 g (3.5 mol) of hydroxylamine hydrochloride. After stirring at 110° C. for 2 hours, the mixture was cooled to 20° C., stirred into 1 kg of ice and rendered alkaline with solid $K_2CO_3$. It was then extracted with ethyl acetate, the combined extracts were extracted with 2N HCl solution and the combined aqueous extracts were rendered alkaline with solid $K_2CO_3$ and again extracted three times with 300 ml of ethyl acetate each time. After concentrating the combined organic extracts, 62 g of ethyl 2-phenyl-4-methylnicotinate (88.5% of theory) were obtained as a yellowish oil, $n_D^{23}$=1.5724.

EXAMPLE 2

4-Methyl-5H-indeno[3,2-b]pyridin-5-ol

A solution of 15 g (0.0769 mol) of 4-methyl-5H-indeno[3,2-b]pyridin-5-one in 150 ml of methanol was treated in portions with 3.8 g (0.1 mol) of $NaBH_4$ at from 0° to –5° C. After stirring at room temperature for 14 hours, the mixture was concentrated under reduced pressure. The residue was treated with 350 ml of methylene chloride and with 150 ml of a 15% strength aqueous potassium hydroxide solution and additionally stirred for 1 hour. The organic phase was separated off, washed with water, dried over $Na_2SO_4$ and concentrated to a volume of 50 ml under reduced pressure. The crystal magma was filtered off with suction at 0° C. and washed with a little diethyl ether and pentane. 9.4 g (62% of theory) of 4-methyl-5H-indeno[3,2-b]pyridin-5-ol were obtained as yellowish crystals of m.p. 154°–156° C.

EXAMPLE 3

4-Methyl-5H-indeno[3,2-b]pyridin-5-one-N-oxide

A solution of 12.7 g (0.065 mol) of 4-methyl-5H-indeno[3,2-b]-pyridin-5-one in 550 ml of chloroform was added dropwise at 25° C. to a solution of 13 g (0.066 mol) of water-moist 3-chloroperbenzoic acid in 500 ml of chloroform. After stirring at room temperature for 12 hours, the mixture was washed twice with 50 ml each of a saturated aqueous sodium hydrogen carbonate solution and then with water, dried over $Na_2SO_4$ and concentrated under reduced pressure. The residue was crystallized at 0° C. using 20 ml of diethyl ether. 12.4 g (90.5% of theory) of 4-methyl-5H-indeno[3,2-b]pyridin-5-one-N-oxide were obtained as white crystals of m.p. 218°–220° C.

EXAMPLE 4

4-Methyl-7-nitro-5H-indeno[3,2-b]pyridin-5-one

A mixture of 35.2 ml of 98.9% strength sulfuric acid with 35.2 ml of 99% strength nitric acid was added dropwise at from +5° to 10° C. to a solution of 15.6 g (0.08 mol) of 4-methyl-5H-indeno[3,2-b]-pyridin-5-one in 35.2 ml of conc. sulfuric acid in the course of 1 hour. After stirring at 25° C. for 14 hours and additionally stirring at 70° C. for 4 hours, the mixture was cooled to 20° C., stirred into 500 g of ice and brought to pH 10 with a 50% strength aqueous sodium hydroxide solution. The mixture was extracted with ethyl acetate, the combined extracts were concentrated under reduced pressure and the residue was crystallized at +10° C. using 30 ml of ether. 13 g (67% of theory) of 4-methyl-7-nitro-5H-indeno[3,2-b]pyridin-5-one were obtained as yellow crystals of m.p. 225°–227° C.

EXAMPLE 5

2-Acetyl-4-methyl-5H-indeno[3,2-b]pyridin-5-one 500 ml of water, 20 g (0.2 mol) of conc. sulfuric acid, 26.4 g (0.3 mol) of pyruvic acid, 1.7 g (0.01 mol) of silver nitrate and 34.2 g (0.15 mol) of ammonium peroxodisulfate were added in succession at 25° C. to a solution of 19.5 g (0.1 mol) of 4-methyl-5H- indeno[3,2-b]pyridin-5-one in 500 ml of methylene chloride. After stirring at 40° C. for 4 hours, the mixture was cooled to +10° C. and rendered alkaline with solid potassium carbonate, and the organic phase was separated off, washed with water and concentrated under reduced pressure. 7.7 g (32.4% of theory) of 2-acetyl-4-methyl-5H-indeno[3,2-b]pyridin-5-one were obtained as pale yellow crystals of m.p. 170°–172° C.

EXAMPLE 6

2,4-Dimethyl-5H-indeno[3,2-b]pyridin-5-one

A solution of 23.6 g (0.24 mol) of 4-amino-3-penten-2-one, 29.2 g (0.2 mol) of indene-1,3-(2H)dione and 7.7 g (0.1 mol) of ammonium acetate in 500 ml of acetic acid was stirred at 115° C. for 3 hours and concentrated under reduced pressure, and the residue was treated with 500 ml of water and rendered alkaline with solid potassium carbonate. The mixture was extracted three times with methylene chloride, and the combined extracts were washed with 100 ml of water and concentrated under reduced pressure. The residue was crystallized at +5° C. using 20 ml of diethyl ether. 10.2 g of 2,4-dimethyl-5H-indeno[3,2-b]pyridin-5- one were obtained as slightly yellow crystals of m.p. 102°–104° C.

EXAMPLE 7

2-Ethyl-4-methyl-5H-indeno[3,2-b]pyridin-5-one

At 25° C., 3.6 g of silver nitrate (0.018 mol) and 26.4 g (0.3 mol) of propionic acid and, at 70° C. in the course of 40 minutes, a solution of 27.4 g (0.12 mol) of ammonium peroxodisulfate in 60 ml of water were added dropwise to a solution of 11.7 g (0.006 mol) of 4-methyl-5H-indeno[3,2-b]pyridin-5-one in 130 ml of 2N sulfuric acid. The mixture was stirred at 80° C. for a further 90 minutes, then cooled and rendered alkaline at about 10° C. with a 28% strength aqueous ammonia solution and extracted three times with methylene chloride, and the combined organic extracts were washed with 50 ml of water and concentrated. The residue was crystallized at 0° C. using 5 ml of diethyl ether. 5.6 g (41.8% of theory) of 2-ethyl-4-methyl-5H-indeno[3,2-b] pyridin-5-one were obtained as slightly yellow crystals of m.p. 68°–70° C.

EXAMPLE 8

4-Methyl-5H-indeno[3,2-b]pyridine 5-O-methyl oxime 11.1 g (0.14 mol) of pyridine were added dropwise to a solution of 13 g (0.066 mol) of 4-methyl-5H-indeno[3,2-b]pyridin-5-one and 12 g (0.14 mol) of O-methylhydroxylamine hydrochloride in 150 ml of methanol. The mixture was stirred for 12 hours at room temperature and for a further 5 hours at 50° C., and was cooled and concentrated under reduced pressure. The residue was dissolved in 300 ml of methylene chloride, and the solution was washed three times with water, dried over $Na_2SO_4$ and concentrated under reduced pressure. 6.3 g (42.6% of theory) of 4-methyl-5H-indeno[3,2-b]-pyridine 5-O-methyl oxime were obtained as white crystals of m.p. 94°–95° C.

EXAMPLE 9 a) 1,3-Dimethyl-4-carboxymethyl-9H-indeno[2,3-b]pyridin-9-one 50 g (0.167 mol) of 2,6-dimethyl-4-phenyl-3,5-bis(carboxymethyl)pyridine and 395 g of polyphosphoric acid were stirred at 170° C. for 3 days, cooled to 50° C., diluted with 800 g of ice and rendered alkaline with a 28% strength aqueous ammonia solution. The mixture was extracted twice with methylene chloride and the combined extracts were concentrated under reduced pressure. The title compound was obtained as yellow crystals of m.p. 152°–154° C. Yield 7.8 g (17.4% of theory).

b) Preparation of 2,6-dimethyl-4-phenyl-3,5-bis(carboxymethyl)-pyridine 90.3 g (0.3 mol) of 1,4-dihydro-2,6-dimethyl-4-phenyl-3,5-bis(carboxymethyl)pyridine were added in portions at from 92° to 98° C. to a solution of 375 g of 98% strength nitric acid in 1580 ml of water in the course of 30 minutes. After a further 30 minutes at 95°–98° C., the mixture was cooled to +5° C. and brought to pH 9 with solid potassium carbonate. The mixture was extracted three times with methylene chloride, the combined extracts were concentrated under reduced pressure and the residue was crystallized at 0° C. using 1:1 diethyl ether/pentane (50 ml). 58.8 g (65.5% of theory) of 2,6-dimethyl-4-phenyl-3,5-bis(carboxymethyl)pyridine were obtained as white crystals of m.p. 137°–138° C.

The compounds of the general formula I/Ia listed in Table 2 were obtained in a similar manner to Preparation Examples 1 to 9 and according to the general directions for preparation:

TABLE 2

Indenopyridines of the formula I

| Ex. No. | $R^1$ | $R^2$ | $R^3$ | $R^4$ | $R^5$ | X | Y | Z | M.p. [°C.] |
|---|---|---|---|---|---|---|---|---|---|
| 10 | H | H | H | H | H | $N^+$—$O^-$ | CH | CH—OH | 203–206 |
| 11 | H | H | H | H | H | N | CH | C=N—O—$CH_2$CH=$CH_2$ | 83–84 |
| 12 | H | H | H | H | H | $N^+$—$O^-$ | CH | C=N—O—$CH_2$CH=$CH_2$ | 129–131 |
| 13 | H | H | H | H | H | N | CH | C=N—O—$CH_2$C≡CH | 159–160 |
| 14 | H | H | H | H | H | N | CH | C=N—O—$CH_2$C(Br)=$CH_2$ | 82–85 |
| 15 | H | H | H | H | H | $N^+$—$O^-$ | CH | C=N—O—$CH_2$C(Br)=$CH_2$ | 135–138 |
| 16 | H | H | H | H | H | N | CH | C=N—$OC_4H_9$-iso | 72–74 |
| 17 | H | H | H | H | H | $N^+$—$O^-$ | CH | C=N—$OC_4H_9$-iso | 118–120 |
| 18 | H | H | H | H | H | N | CH | C=N—O—$CH_2$C($CH_3$)=$CH_2$ | 55–57 |
| 19 | H | H | H | H | H | N | CH | C=N—O—$C_6H_{13}$-n | 30–33 |
| 20 | H | H | H | H | H | N | CH | C=N—O—$CH_2COOCH_3$ | 144–146 |
| 21 | H | H | H | H | H | $N^+$—$O^-$ | CH | C=N—O—$CH_2COOCH_3$ | 163–165 |
| 22 | H | H | H | H | H | N | CH | C=N—$OCH_2COOC_4H_9$-tert | 129–131 |
| 23 | H | H | H | H | H | N | CH | C=N—$OCH_2$—$C_6H_5$ | 103–105 |
| 24 | H | H | H | H | H | $N^+$—$O^-$ | CH | C=N—$OCH_2$—$C_6H_5$ | 142–144 |
| 25 | H | H | H | H | H | N | CH | C=N—$O(CH_2)_3C_6H_5$ | 77–79 |
| 26 | H | H | H | H | H | $N^+$—$O^-$ | CH | C=N—$(CH_2)_3C_6H_5$ | 97–98 |
| 27 | H | H | H | H | H | $N^+$—$O^-$ | CH | C=N—$OCH_2C_6H_4$-4F | 167–169 |
| 28 | H | H | H | H | H | N | CH | C=N—$OCH_2C_6H_4$-4F | 81–83 |
| 29 | H | H | H | H | H | N | CH | C=N—$OCH_2C_6H_4$-4Cl | 112–114 |
| 30 | H | H | H | H | H | $N^+$—$O^-$ | CH | C=N—$OCH_2C_6H_4$-4Cl | 186–188 |
| 31 | H | H | H | H | H | N | CH | C=N—$OCH_2CH_2C_6H_4$-4Cl | 121–123 |
| 32 | H | H | H | H | H | $N^+$—$O^-$ | CH | C=N—$OCH_2CH_2C_6H_4$-4Cl | 182–184 |
| 33 | H | H | H | H | H | N | CH | C=N—$OCH_2$—$C_6H_4$-$2CH_3$ | 108–110 |
| 34 | H | H | H | H | H | $N^+$—$O^-$ | CH | C=N—$OCH_2$—$C_6H_4$-$2CH_3$ | 130–131 |
| 35 | H | H | H | H | H | N | CH | C=N—$OCH_2$—$C_6H_4$-$3CH_3$ | 56–58 |
| 36 | H | H | H | H | H | N | CH | C=N—$OCH_2$—$C_6H_4$-$4OCH_3$ | 73–77 |
| 37 | H | H | H | H | H | N | CH | C=N—$OCH_2C_6H_3$-3,4$Cl_2$ | 114–116 |
| 38 | H | H | H | H | H | $N^+$—$O^-$ | CH | C=N—$OCH_2C_6H_3$-3,4$Cl_2$ | 205–207 |
| 39 | H | H | H | H | H | N | CH | C=NO—$CH_2C_6H_3$-3Cl-4CH($CH_3)_2$ | 118–120 |
| 40 | H | H | H | H | H | $N^+$—$O^-$ | CH | C=NO—$CH_2C_6H_3$-2Cl-3CH($CH_3)_2$ | 128–130 |
| 41 | H | H | H | H | H | N | CH | C=NO—$CH_2C_6H_3$-3Cl-4CH($CH_3)_2$ | 125–127 |
| 42 | H | H | H | H | H | N | CH | C=N—O—$CH_2CH_2C_6H_5$ | 82–84 |
| 43 | H | H | H | H | H | N | CH | C=N—O—$CH_2$(3-thienyl) | 93–95 |
| 44 | H | H | H | H | H | N | CH | C=N—O—$CH_2$(5-Cl-3-thienyl) | 118–120 |
| 45 | H | H | H | H | H | N | CH | C=N—O—$CH_2$(5Cl-2-thienyl) | 124–126 |
| 46 | H | H | H | H | H | N | CH | C=$NOCH_2$(3$CH_3$-5-isoxazolyl) | 126–128 |
| 47 | H | H | H | H | H | N | CH | C=O | 136–139 |
| 48 | H | H | H | H | F | N | CH | C=O | 174–176 |
| 49 | H | H | H | H | H | N | CH | CH—OH | 153–156 |
| 50 | H | H | Cl | H | H | N | CH | C=O | 132–134 |
| 51 | H | H | Cl | H | H | N | CH | CH—OH | 193–195 |
| 52 | H | H | Cl | H | H | $N^+$—$O^-$ | CH | C=O | 105–107 |
| 53 | H | H | Cl | H | H | N | CH | C=N—$OCH_3$ | 130–132 |
| 54 | H | H | Cl | H | H | N | CH | C=N—$OC_2H_5$ | 81–83 |

TABLE 2-continued

Indenopyridines of the formula I

| Ex. No. | R¹ | R² | R³ | R⁴ | R⁵ | X | Y | Z | M.p. [°C.] |
|---|---|---|---|---|---|---|---|---|---|
| 55 | H | H | Cl | H | H | N | CH | C=N—O—CH$_2$CH=CHCl | 129–131 |
| 56 | H | H | Cl | H | H | N | CH | C=N—OCH$_2$—COOC$_4$H$_9$-tert | 138–139 |
| 57 | H | H | Cl | H | H | N | CH | C=N—OCH$_2$C$_6$H$_5$ | 124–126 |
| 58 | H | H | Cl | H | H | N | CH | C=N—O—(CH$_2$)$_3$—C$_6$H$_5$ | 106–108 |
| 59 | H | H | Cl | H | H | N | CH | C=NO(CH$_2$)$_2$CH=CH—C$_6$H$_4$-4Cl | 114–118 |
| 60 | H | H | Cl | H | H | N | CH | C=N—O(CH$_2$)$_6$—C$_6$H$_4$-4Cl | 53–58 |
| 61 | H | H | Cl | H | H | N | CH | C=N—OCH$_2$C$_6$H$_4$-4CH$_3$O | 155–156 |
| 62 | H | H | Cl | H | H | N | CH | C=N—OCH$_2$CH(CH$_3$)CH$_2$C$_6$H$_4$-4Cl | 82–84 |
| 63 | H | H | Cl | H | H | N | CH | C=N—O(CH$_2$)$_2$—(2-thienyl) | 132–133 |
| 64 | H | H | Cl | H | H | N | CH | C=NO(CH$_2$)$_2$CH=CH(5Cl-2-thienyl) | 103–105 |
| 65 | CH$_3$ | H | Cl | H | H | C—COOCH$_3$ | N | C=O | 197–199 |
| 66 | CH$_3$ | H | H | Cl | H | C—COOC$_2$H$_5$ | N | C=O | 147–148 |
| 67 | CH$_3$ | Cl | H | H | H | C—COOC$_2$H$_5$ | N | C=O | 163–164 |
| 68 | H | H | H | H | Cl | C—COOEt | N | C=O | 104–106 |
| 69 | H | H | H | H | Cl | N | CH | C=O | 158–159 |
| 70 | H | H | H | H | Cl | N | CH | CH—OH | 192–194 |
| 71 | H | H | CH$_3$ | H | H | N | CH | C=O | 108–109 |
| 72 | H | H | H | H | CH$_3$ | N | CH | C=O | 116–118 |
| 73 | H | H | H | H | CH$_3$ | N | CH | C=N—O—CH$_2$C$_6$H$_5$ | 88–90 |
| 74 | H | H | CH(CH$_3$)$_2$ | H | H | N | CH | C=O | 87–89 |
| 75 | H | H | CH(CH$_3$)$_2$ | H | H | N | CH | CH—OH | 164–165 |
| 76 | H | H | CH(CH$_3$)$_2$ | H | H | N | CH | C=N—OCH$_3$ | 88–91 |
| 77 | H | H | CH(CH$_3$)$_2$ | H | H | N | CH | C=N—OC$_2$H$_5$ | 58–63 |
| 78 | H | H | CH(CH$_3$)$_2$ | H | H | N | CH | C=NOCH$_2$CH(CH$_3$)—CH$_2$C$_6$H$_4$-4Cl | Öl |
| 79 | H | H | CH(CH$_3$)$_3$ | H | H | N | CH | C=O | 93–96 |
| 80 | H | H | CH(CH$_3$)$_3$ | H | H | N | CH | CH—OH | 204–206 |
| 81 | H | H | CH(CH$_3$)$_3$ | H | H | N | CH | C=N—OC$_2$H$_5$ | 107–112 |
| 82 | H | H | CH(CH$_3$)$_3$ | H | H | N | CH | C=NOCH$_2$CH(CH$_3$)—CH$_2$C$_6$H$_4$-4Cl | Öl |
| 83 | H | H | CH(CH$_3$)$_2$ | H | H | N | CH | C=N—OCH$_2$CH=CH—Cl | 103–105 |
| 84 | H | H | C$_6$H$_5$ | H | H | N | CH | C=O (hydrochloride) | >200 |
| 85 | H | H | C$_6$H$_5$ | H | H | N | CH | CH—OH | 183–186 |
| 86 | H | H | C$_6$H$_5$ | H | H | N | CH | CH=N—OCH$_3$ | 142–144 |
| 87 | H | H | C$_6$H$_5$ | H | H | N | CH | C=N—OC$_2$H$_5$ | 115–117 |
| 88 | H | H | CH$_3$O— | H | H | N | CH | C=O | 138–140 |
| 89 | H | H | NO$_2$ | H | H | N⁺—O⁻ | CH | C=O | 262 |
| 90 | H | H | CF$_3$ | H | H | N | CH | C=O | 132–135 |
| 91 | H | H | Cl | Cl | H | N | CH | C=O | >200 |
| 92 | H | H | Cl | Cl | H | N | CH | C=O | 203–205 |
| 93 | H | H | Cl | H | Cl | N | CH | C=O | 193–196 |
| 94 | H | H | Cl | Cl | H | N | CH | C=O | 185–188 |
| 95 | H | H | Cl | Cl | H | N | CH | CH—OH | 181–192 |
| 96 | H | H | Cl | Cl | H | N | CH | C=N—OCH$_3$ | 198–199 |
| 97 | H | H | Cl | Cl | H | N | CH | C=N—OC$_2$H$_5$ | 119–121 |
| 98 | H | H | Cl | Cl | H | N | CH | C=N—OCH$_2$CH=CHCl | 181–182 |
| 99 | H | H | Cl | Cl | H | N | CH | C=NOCH$_2$CH(CH$_3$)—CH$_2$C$_6$H$_4$-4Cl | 210–212 |
| 100 | H | H | Cl | Cl | H | N | CH | C=N—O(CH$_2$)$_2$-(2-thienyl) | 125–126 |
| 101 | H | Cl | H | Cl | H | N | CH | C=N—OCH$_2$CH=CHCl | 173–175 |
| 102 | H | H | CONH$_2$ | H | H | N | CH | C=O | >200 |
| 103 | H | H | NO$_2$ | H | H | N | CH | C=N—O—CH$_2$—C$_6$H$_5$ | 154–157 |
| 104 | H | H | H | H | H | N | CH | CH—NH$_2$ | 104–106 |
| 105 | H | H | H | H | H | N | CH | CH—OCOCH$_3$ | 106–108 |
| 106 | H | H | H | H | H | N | CH | CH—OCOCH$_2$CH$_3$ | 79–81 |
| 107 | H | H | H | H | H | N | CH | CH—OCO—C$_6$H$_5$ | 143–145 |
| 108 | H | H | H | H | F | N | CH | CH—OH | 201–203 |
| 109 | H | H | H | H | F | N | CH | CH—OCOCH$_3$ | 129–130 |
| 110 | H | H | H | H | H | N | CH | C=N—NH$_2$ | 203–205 |
| 111 | H | H | H | H | H | N | CH | C=N—NH—C$_6$H$_5$ | 185–187 |
| 112 | H | H | C$_6$H$_{11}$ | H | H | N | CH | C=N—OCH$_3$ | 120–121 |
| 113 | H | H | C$_6$H$_{11}$ | H | H | N | CH | CHOH | 212–215 |
| 114 | H | H | Br | H | H | N | CH | CHOH | 197–200 |
| 115 | H | H | H | H | H | N | CH | CHOCOC$_3$H$_7$ | 70–72 |
| 116 | H | H | H | H | H | N | CH | CHOCOCH(CH$_3$)$_2$ | 97–89 |
| 117 | H | H | H | H | H | N | CH | CHOCOCH$_2$CH(CH$_3$)$_2$ | |
| 118 | H | H | H | H | H | N | CH | CHOCOC$_5$H$_{11}$ | 50–52 |
| 119 | H | H | H | H | H | N | CH | CHOCOC$_6$H$_{13}$ | |
| 120 | H | H | H | H | H | N | CH | C=NOCH$_3$ | 94–95 |
| 121 | H | H | Cl | H | H | N | CH | C=NOCH$_3$ | 130–132 |
| 122 | H | H | Cl | H | H | N | CH | C=NOCH$_2$C$_6$H$_5$—pOCH$_3$ | 155–156 |
| 123 | H | H | H | H | H | N | CH | C=NOCH(CH$_3$)$_2$ | 54–55 |
| 124 | H | Cl | H | Cl | H | N | CH | C=NOCH$_2$CH=CHCl | 173–175 |
| 125 | H | H | C$_6$H$_5$ | H | H | N | CH | C=NOC$_2$H$_5$ | 115–117 |
| 126 | H | H | CH(CH$_3$)$_2$ | H | H | N | CH | C=NOCH$_2$CH=CHCl | 103–105 |
| 127 | H | H | CH(CH$_3$)$_2$ | H | H | N | CH | C=NOCH$_2$-(2-thienyl) | Oil |
| 128 | H | H | H | H | H | N | CH | C=NOCH$_2$C$_6$H$_3$-3Cl-4CH(CH$_3$)$_2$ | 118–120 |

TABLE 2-continued

Indenopyridines of the formula I

| Ex. No. | R¹ | R² | R³ | R⁴ | R⁵ | X | Y | Z | M.p. [°C.] |
|---|---|---|---|---|---|---|---|---|---|
| 129 | H | H | C₆H₅ | H | H | N | CH | C=NOCH₂C₆H₅ | 114–118 |
| 130 | H | H | H | H | H | N | CH | C=NOCH₂C₆H₃-2-Br-3CH(CH₃)₂ | 125–127 |
| 131 | H | H | Cl | H | H | N | CH | C=NOCH₂C₆H₅ | 124–126 |
| 132 | H | H | H | H | H | N | CH | C=NOCH₂(4-Oxazolyl-2(4'-bromophenyl) | 148–150 |
| 133 | H | H | H | H | H | N | CH | C=N—NH—C₆H₄-4-OCH₃ | 267–268 |
| 134 | H | H | H | H | H | N | CH | C=N—NH—C₆H₃-2,6-Cl | 199–200 |
| 135 | H | H | H | H | H | N | CH | C=N—NH—CH₃C₆H₅ | 129–131 |
| 136 | H | H | H | H | H | N | CH | C=N—NH—C₆H₃-2,5-Cl | 222–224 |
| 137 | H | H | Br | H | H | N | CH | C=NOCH₃ | 153–155 |
| 138 | H | H | Br | H | H | N | CH | C=NOCH₂CH=CHCl | 143–145 |
| 139 | H | H | Br | H | H | N | CH | C=NOCH₂C₆H₄-2-CH₃ | 131–133 |
| 140 | H | H | Br | H | H | N | CH | C=NOCH₂C₆H₅ | 123–125 |
| 141 | H | H | NO₂ | H | H | N | CH | C=N—NH₂ | 231–233 |
| 142 | H | H | H | H | Cl | N | CH | C=O | 158–159 |
| 143 | COCH₃ | H | H | H | H | N | CH | C=O | 170–172 |
| 144 | H | H | NO₂ | H | H | N | CH | C=O | 225–227 |
| 145 | CH₃ | H | H | H | H | N | CH | C=O | 102–104 |
| 146 | H | H | H | H | CH₃ | N | CH | C=O | 116–118 |
| 147 | C₂H₅ | H | H | H | H | N | CH | C=O | 68–70 |
| 148 | H | H | F | H | H | N | CH | C=O | 142–144 |
| 149 | H | Cl | Cl | H | H | N | CH | C=O | 185–188 |
| 150 | H | H | C₆H₁₁ | H | H | N | CH | C=O | 90–93 |
| 151 | H | H | Br | H | H | N | CH | C=O | 138–140 |
| 152 | H | H | NH₂ | H | H | N | CH | C=O | 194–196 |
| 153 | H | H | H | H | H | N⊕—O⊖ | CH | C=O | 218–220 |
| 154 | H | H | H | H | H | N⊕—O⊖ | CH | C=N—OCH₂C₆H₄-2-Cl, 3-CH(CH₃)₂ | 128–130 |
| 155 | CH₃ | H | H | H | H | C—COOCH₃ | N | C=O | 152–154 |
| 156 | CH₃ | H | H | H | H | C—COOH | N | C=O | 250 |

USE EXAMPLES

It was possible to show the herbicidal action of the indenopyridines of the formula I or Ia by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth and then covered with transparent plastic hoods until the plants had taken root. This covering causes uniform germination of the test plants if this has not been adversely affected by the active compounds.

For the purposes of post-emergence treatment, the test plants, depending on growth form, were first treated with the active compounds suspended or emulsified in water at a height of growth of from 3 to 15 cm. The application rate for post-emergence treatment was from 0.5 to 3.0 kg/ha of a.s.

The plants were kept species-specifically at 10°–25° C. or 20°–35° C. The test period extended over 2 to 4 weeks. During this time, the plants were tended and their reaction to the individual treatments was assessed.

Assessment was carried out on a scale of from 0 to 100. 100 here means no emergence of the plants or complete destruction of at least the above-ground parts and 0 means no damage or normal course of growth.

The plants used in the greenhouse tests were made up of the following species:

| Botanical name | Common name |
|---|---|
| Bromus spp. | brome |
| Centaurea cyanus | cornflower |
| Echinochloa crus-galli | barnyardgrass |
| Setaria italica | millet foxtail |
| Digitaria sanguinalis | large crabgrass |
| Brassica napus | oilseed rape |

The results (see Tables I–III) confirm the superior herbicidal action of compound No. 48 according to the invention in comparison with the following comparison compounds known from the prior art:

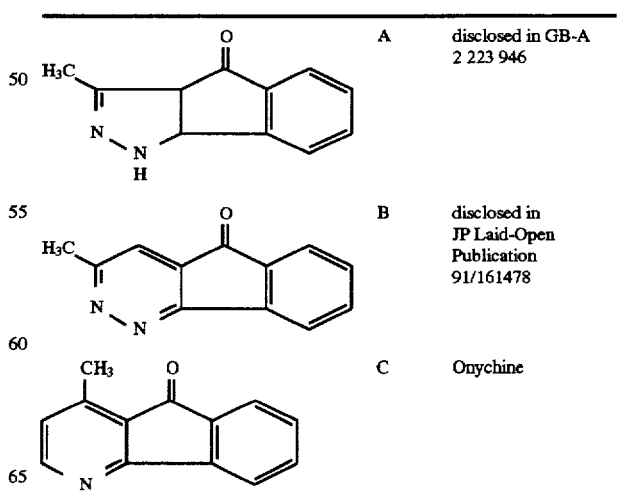

A  disclosed in GB-A 2 223 946

B  disclosed in JP Laid-Open Publication 91/161478

C  Onychine

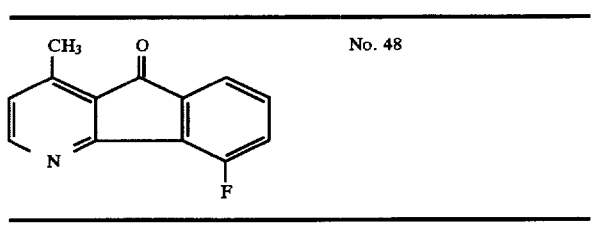

In the exemplary crop winter rape, compound No. 11 showed a very good growth-inhibiting action at an application rate of 0.5 kg/ha. At an application rate of 0.5 kg/ha of a.s., compound No. 75 showed a good herbicidal action and simultaneously had high selectivity in the crops spring wheat and cotton.

TABLE I

Examples of the control of undesired plants in the case of post-emergence application of 3.0 kg of a.s./ha in the greenhouse

| | Damage in % | |
|---|---|---|
| Test plants | Ex. No. 48 | A |
| Bromus spp. | 100 | 15 |
| Centaurea cyanus | 100 | 0 |
| Echinochloa crus-galli | 100 | 40 |

TABLE II

Examples of the control of undesired plants in the case of post-emergence application in the greenhouse

| | Damage in % | |
|---|---|---|
| Ex.-No. | 48 | B |
| Application rate (kg of a.s./ha) | 1.0 | 1.5 |
| Test plants | | |
| Centaurea cyanus | 95 | 20 |
| Echinochloa crus-galli | 84 | 0 |
| Setaria italica | 100 | 85 |

TABLE III

Examples of the control of undesired plants in the case of post-emergence application in the greenhouse

| | Damage in % | | | |
|---|---|---|---|---|
| Ex.-No. | 48 | 48 | C | C |
| Application rate (kg a.s./ha) | 1.0 | 0.5 | 1.0 | 0.5 |
| Test plants | | | | |
| Centaurea cyanus | 95 | 50 | 50 | 20 |
| Digitaria sanguinalis | 100 | 100 | 90 | 60 |
| Echinochloa crus-galli | 90 | 60 | 40 | 40 |

We claim:

1. A 4-Methyl-5H-indeno[3,2-b]pyridine or 1-methyl-9H-indeno-[2,3-c]pyridine of the general formula I

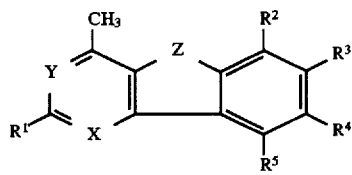

where X, Y, Z and the radicals $R^1$ to $R^5$ have the following meanings:

$R^1$ is hydrogen, $C_1$-$C_6$-alkyl or a $COR^6$ group, $R^6$ being $C_1$-$C_4$-alkyl, $R^2$-$R^5$ are
a) hydrogen,
b) halogen,
c) nitro,
d) $COOR^6$, $R^6$ being $C_1$-$C_4$-alkyl,
e) $CONH_2$ or $CONR^6R^7$, $R^6$ and $R^7$ being $C_1$-$C_4$-alkyl,
f) $C_1$-$C_8$-alkyl which can carry one to three of the following substituents: halogen, hydroxyl or $C_1$-$C_6$-alkoxy,
g) $C_3$-$C_6$-alkenyl,
h) $C_1$-$C_4$-alkoxy,
i) hydroxyl,
j) amino or $NR^6R^7$,
k) phenyl which can carry one to five halogen atoms or one to three of the following substituents: nitro, $C_1$-$C_4$-alkoxy, $C_1$-$C_4$-alkyl or $C_1$-$C_4$-haloalkyl;

X is N or $N^+$—$O^-$;

Y is $CR^8$, $R^8$ being hydrogen, $C_1$-$C_2$-alkyl, COOH or $COOR^6$;

Z is a C=O, CH—$OR^9$, CH—O—$COR^9$ or C=N—W—$R^9$ group, W being oxygen or the —$N(R^{10})$ group and where $R^9$ is hydrogen, a $C_1$-$C_6$-alkyl group which can be substituted by halogen, $COOR^6$ or $C_1$-$C_4$-alkoxy, a $C_3$-$C_6$-alkenyl group, a $C_3$-$C_6$-haloalkenyl group, a $C_3$-$C_6$-alkynyl group, or phenyl, phenyl-$C_1$-$C_4$-alkyl or mononuclear heteroaryl or heteroaryl-$C_1$-$C_4$-alkyl radicals, these aromatic or heteroaromatic groups being able to carry one to three of the following substituents on the ring: halogen, nitro, $C_1$-$C_6$-alkyl, $C_1$-$C_6$-alkoxy, $C_1$-$C_2$-haloalkyl, amino, $C_1$-$C_6$-alkylamino or di($C_1$-$C_6$-alkyl)amino and $R^{10}$ is hydrogen or a $C_1$-$C_4$-alkyl group, and the salts of I with those acids which do not adversely affect the herbicidal or the plant growth-regulating action of I, excluding onychine, dihydroonychine, 6-, 7-, 8- and 9-methoxyonychine, 6-, 7-, 8- and 9-hydroxyonychine, 7,8-dimethoxyonychine, 4-methyl-5H-indeno[3,2-b]pyridines of the formula Ia

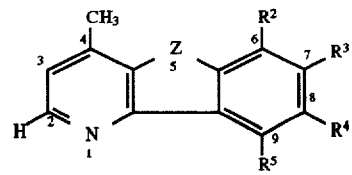

where two of the radicals $R^2$, $R^3$, $R^4$ and $R^5$ form a combination of methoxy and hydroxyl if Z is C=O or CHOH and the remaining two radicals are hydrogen or methoxy, and 4-methyl-5H-indeno[3,2-b] pyridines of formula Ia where three of the radicals $R^2$, $R^3$, $R^4$, $R^5$ are hydrogen, the remaining radical is methyl.

2. A herbicidal composition, containing a herbicidally effective amount of a compound of the formula I as defined in claim 1.

3. A composition for regulating plant growth, containing a bioregulatory amount of a compound of the formula I as defined in claim 1, and inert additives.

4. A method for controlling undesired plant growth, which comprises allowing a herbicidally effective amount of a compound of the formula I

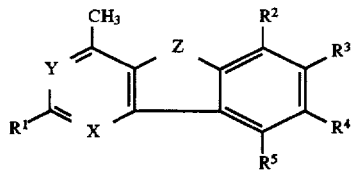

where X, Y, Z and the radicals $R^1$ to $R^5$ have the following meanings:

$R^1$ is hydrogen, $C_1$-$C_6$-alkyl or a $COR^6$ group, $R^6$ being $C_1$-$C_4$-alkyl, $R^2$-$R^5$ are
a) hydrogen,
b) halogen,
c) nitro,
d) $COOR^6$, $R^6$ being $C_1$-$C_4$-alkyl,
e) $CONH_2$ or $CONR^6R^7$, $R^6$ and $R^7$ being $C_1$-$C_4$-alkyl,
f) $C_1$-$C_8$-alkyl which can carry one to three of the following substituents: halogen, hydroxyl or $C_1$-$C_6$-alkoxy,
g) $C_3$-$C_6$-alkenyl,
h) $C_1$-$C_4$-alkoxy,
i) hydroxyl,
j) amino or $NR^6R^7$,
k) phenyl which can carry one to five halogen atoms or one to three of the following substituents: nitro, $C_1$-$C_4$-alkoxy, $C_1$-$C_4$-alkyl or $C_1$-$C_4$-haloalkyl;

X and Y are N, $N^+$—$O^-$ or $CR^8$, $R^8$ being hydrogen, $C_1$-$C_2$-alkyl, COOH or $COOR^6$, with the proviso that exclusively one nitrogen atom or one N-oxide group is contained in the ring;

Z is a C=O, CH—$OR^9$, CH—O—$COR^9$ or C=N—W— $R^9$ group, W being oxygen or the —$N(R^{10})$ group and where $R^9$ is hydrogen, a $C_1$-$C_6$-alkyl group which can be substituted by halogen, $COOR^6$ or $C_1$-$C_4$-alkoxy, a $C_3$-$C_6$-alkenyl group, a $C_3$-$C_6$-haloalkenyl group, a $C_3$-$C_6$-alkynyl group, or phenyl, phenyl-$C_1$-$C_4$-alkyl or mononuclear heteroaryl or heteroaryl-$C_1$-$C_4$-alkyl radicals, these aromatic or heteroaromatic groups being able to carry one to three of the following substituents on the ring: halogen, nitro, $C_1$-$C_6$-alkyl, $C_1$-$C_6$-alkoxy, $C_1$-$C_2$-haloalkyl, amino, $C_1$-$C_6$-alkylamino or di($C_1$-$C_6$-alkyl)amino and $R^{10}$ is hydrogen or a $C_1$-$C_4$-alkyl group, and the salts of I with those acids which do not adversely affect the herbicidal or the plant growth-regulating action of I to act on plants, their habitat or on seeds.

5. A compound of the formula I as set forth in claim 1, wherein $R^1$, $R^2$, $R^3$ and $R^4$, are hydrogen, $R^5$ is fluorine, X is N, Y is CH and Z is C=O.

6. A method defined in claim 4, wherein the compound of the formula I $R^1$, $R^2$, $R^3$ and $R^4$, are hydrogen, $R^5$ is fluorine, X is N, Y is CH and Z is C=O.

* * * * *

UNITED STATES PATENT AND TRADEMARK OFFICE
CERTIFICATE OF CORRECTION

PATENT NO.: 5,637,554

DATED: June 10, 1997

INVENTOR(S): RENTZEA et al.

It is certified that error appears in the above-identified patent and that said Letters Patent is hereby corrected as shown below:

Column 35, claim 1, line 67, delete "general".

Signed and Sealed this

Twelfth Day of August, 1997

Attest:

BRUCE LEHMAN

*Attesting Officer*     *Commissioner of Patents and Trademarks*